US008293702B2

(12) United States Patent
Murray et al.

(10) Patent No.: US 8,293,702 B2
(45) Date of Patent: Oct. 23, 2012

(54) PHENOLIC BINDING PEPTIDES

(75) Inventors: Christopher J. Murray, Soquel, CA (US); Pilar Tijerina, Austin, TX (US); Franciscus J. C. Van Gastel, Union City, CA (US); Giselle G. Janssen, Dixon, CA (US)

(73) Assignee: Danisco US Inc., Palo Alto, CA (US)

( * ) Notice: Subject to any disclaimer, the term of this patent is extended or adjusted under 35 U.S.C. 154(b) by 1157 days.

(21) Appl. No.: 12/144,572

(22) Filed: Jun. 23, 2008

(65) Prior Publication Data
US 2009/0081178 A1    Mar. 26, 2009

Related U.S. Application Data

(63) Continuation of application No. 10/528,514, filed as application No. PCT/US03/31776 on Oct. 6, 2003.

(60) Provisional application No. 60/417,210, filed on Oct. 8, 2002.

(51) Int. Cl.
| A61K 38/00 | (2006.01) |
| A61K 38/04 | (2006.01) |
| A61K 51/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. .................. 514/1.1; 530/329; 424/1.69
(58) Field of Classification Search ............... None
See application file for complete search history.

(56) References Cited

U.S. PATENT DOCUMENTS

| 3,929,678 | A | 12/1975 | Laughlin et al. | 252/526 |
| 4,689,297 | A | 8/1987 | Good et al. | |
| 4,760,025 | A | 7/1988 | Estell et al. | 435/222 |
| 5,011,681 | A | 4/1991 | Ciotti et al. | 424/81 |
| 5,770,419 | A | 6/1998 | Feng et al. | 435/189 |
| 5,985,818 | A | 11/1999 | Svendsen et al. | 510/392 |
| 5,989,899 | A | 11/1999 | Bower et al. | 435/263 |
| 6,060,442 | A | 5/2000 | Svendsen | 510/392 |
| 6,063,611 | A | 5/2000 | Van Solingen | 435/209 |
| 6,110,884 | A | 8/2000 | Rasmussen et al. | 510/392 |
| 6,156,552 | A | 12/2000 | Okkels et al. | 435/198 |
| 6,168,936 | B1 | 1/2001 | Wang | 435/189 |
| 6,171,345 | B1 | 1/2001 | Convents et al. | 8/137 |
| 6,190,900 | B1 | 2/2001 | Sierkstra et al. | 435/221 |
| 6,197,567 | B1 | 3/2001 | Aaslyng et al. | 435/221 |
| 6,268,328 | B1 | 7/2001 | Mitchinson et al. | 510/392 |
| 6,287,839 | B1 | 9/2001 | Jones et al. | 435/209 |
| 6,348,317 | B1 | 2/2002 | Thompson et al. | |
| 6,352,968 | B1 | 3/2002 | Convents et al. | 510/320 |
| 6,423,524 | B1 | 7/2002 | Hagen et al. | 435/200 |
| 6,440,716 | B1 | 8/2002 | Svendsen et al. | 435/202 |
| 2002/0098524 | A1 | 7/2002 | Murray et al. | 435/7.9 |
| 2003/0152976 | A1 | 8/2003 | Janssen et al. | 435/6 |

FOREIGN PATENT DOCUMENTS

| EP | 260105 | 3/1988 |
| EP | 251446 | 7/1988 |
| EP | A-346995 A2 | 12/1989 |
| EP | 0407225 A1 | 9/1991 |
| EP | 0525610 | 3/1993 |
| EP | 130756 B2 | 6/2000 |
| GB | 2094826 A | 9/1982 |
| WO | WO 87/04461 | 7/1987 |
| WO | WO 94/02618 | 3/1994 |
| WO | WO 95/01426 | 1/1995 |
| WO | WO 95/22615 | 8/1995 |
| WO | WO 95/06720 | 9/1995 |
| WO | WO 96/27002 | 6/1996 |
| WO | WO 96/06930 | 7/1996 |
| WO | WO 97/07202 | 2/1997 |
| WO | WO 97/11217 | 3/1997 |
| WO | WO 97/04079 | 6/1997 |
| WO | WO 98/27198 | 12/1997 |
| WO | WO 98/27197 | 6/1998 |
| WO | WO 98/34956 | 8/1998 |
| WO | WO 98/38286 | 9/1998 |
| WO | WO 99/49020 | 9/1999 |
| WO | WO 00/37654 | 6/2000 |
| WO | WO 00/48464 | 8/2000 |
| WO | WO 01/21809 | 3/2001 |
| WO | WO 01/79479 | 10/2001 |
| WO | WO 02/26782 | 4/2002 |
| WO | WO 02/055543 | 7/2002 |
| WO | WO 02/057299 A2 | 7/2002 |

OTHER PUBLICATIONS

Balass et al., "Recovery of High-Affinity Phage from a Nitrostreptavidin Matrix in Phage-Display Technology, *Analytical Biochemistry*," 243:264-269, 1996.

Cwirla et al., "Peptides on phage: A vast library of peptides for identifying ligands," *Proc. Natl. Acad. Sci. USA*, vol. 87, pp. 6378-6382, Aug. 1990.

Huls et al., "A recombinant, fully human monoclonal antibody with antitumor activity constructed from phage-displayed antibody fragments," *Nature Biotechnology*, 17:276-281, Mar. 1999.

Parmley et al., "Antibody-selectable filamentous fd phage vectors: affinity purification of target genes," *Gene*, vol. 73, pp. 305-318, 1988.

Shing Chang et al., "High Frequency Transformation of *Bacillus subtilis* Protoplasts by Plasmid DNA," *Molec. Gen. Genet.*, 168:111-115 (1979).

Maria Helena P. Fungaro et al., "Transformation of *Aspergillus nidulans* by microprojectile bombardment on intact conidia," *FEMS Microbiology Letters*, 125:293-298 (1995).

(Continued)

*Primary Examiner* — Maury Audet
(74) *Attorney, Agent, or Firm* — Danisco US Inc.

(57) ABSTRACT

The present application relates to peptides which bind to tannin, polyphenolic or anthocyanin compounds, and particularly to tea and wine stains on a fabric or other surface. The invention also concerns binding peptide conjugates which includes a binding peptide coupled to an agent and the use of the binding peptide conjugate for delivering an agent to a desired target.

16 Claims, 8 Drawing Sheets

| | | | |
|---|---|---|---|
| KTPSPHG | (SEQ ID NO. 1) | KFMHTTA | (SEQ ID NO. 28) |
| PNTTRHS | (SEQ ID NO. 2) | KTSIGHW | (SEQ ID NO. 29) |
| GKMYLKA | (SEQ ID NO. 3) | LPAKPLA | (SEQ ID NO. 30) |
| NQSHMPR | (SEQ ID NO. 4) | LNSSSKS | (SEQ ID NO. 31) |
| KTPSSME | (SEQ ID NO. 5) | NKSNATV | (SEQ ID NO. 32) |
| IEKPHAD | (SEQ ID NO. 6) | ALNPLHT | (SEQ ID NO. 33) |
| PTYHHQT | (SEQ ID NO. 7) | DTHTQKH | (SEQ ID NO. 34) |
| LWTSPQL | (SEQ ID NO. 8) | TAQIHSV | (SEQ ID NO. 35) |
| HSLDQRS | (SEQ ID NO. 9) | TMAPAKN | (SEQ ID NO. 36) |
| QIQTPLS | (SEQ ID NO. 10) | SHLDKRL | (SEQ ID NO. 37) |
| SLNNTNT | (SEQ ID NO. 11) | TNWDAPT | (SEQ ID NO. 38) |
| VPTGKLQ | (SEQ ID NO. 12) | TMSRVNQ | (SEQ ID NO. 39) |
| PTWSLAM | (SEQ ID NO. 13) | TTTNKPL | (SEQ ID NO. 40) |
| LGTPQQT | (SEQ ID NO. 14) | LTQNFHS | (SEQ ID NO. 41) |
| SFYHQTY | (SEQ ID NO. 15) | NPTQLQN | (SEQ ID NO. 42) |
| MMNSWHK | (SEQ ID NO. 16) | SPTSTNS | (SEQ ID NO. 43) |
| KQSQPQT | (SEQ ID NO. 17) | PGSNATQ | (SEQ ID NO. 44) |
| QKHSPGH | (SEQ ID NO. 18) | SQDTPMY | (SEQ ID NO. 45) |
| TSGSMHS | (SEQ ID NO. 19) | TDPSMMN | (SEQ ID NO. 46) |
| VLRPAAL | (SEQ ID NO. 20) | GQADRLQ | (SEQ ID NO. 47) |
| SPMDEYY | (SEQ ID NO. 21) | TPQRLLT | (SEQ ID NO. 48) |
| LKSTRPT | (SEQ ID NO. 22) | QWTDPMK | (SEQ ID NO. 49) |
| DSRLSRS | (SEQ ID NO. 23) | AKTNLKD | (SEQ ID NO. 50) |
| TNNTSPT | (SEQ ID NO. 24) | EVTTVRN | (SEQ ID NO. 51) |
| QTQPPGS | (SEQ ID NO. 25) | LNNYRNM | (SEQ ID NO. 52) |
| LKNVPFR | (SEQ ID NO. 26) | SQMSPLH | (SEQ ID NO. 53) |
| HNYTLQK | (SEQ ID NO. 27) | SARSLPF | (SEQ ID NO. 54) |
| | | PTHLANM | (SEQ ID NO. 55) |
| | | TQKDDRQ | (SEQ ID NO. 56) |

*FIG. 1A*

| | | | |
|---|---|---|---|
| TDFHQGT | (SEQ ID NO. 57) | NEINAQS | (SEQ ID NO. 84) |
| TYEAPRT | (SEQ ID NO. 58) | PLTSTQP | (SEQ ID NO. 85) |
| LQINAQT | (SEQ ID NO. 59) | PPNSSSS | (SEQ ID NO. 86) |
| HVWSQAW | (SEQ ID NO. 60) | HVSDLAG | (SEQ ID NO. 87) |
| HQGPLRT | (SEQ ID NO. 61) | TLSRTTA | (SEQ ID NO. 88) |
| TQNPTHS | (SEQ ID NO. 62) | INKTMAE | (SEQ ID NO. 89) |
| ENSFAGG | (SEQ ID NO. 63) | HLRSTTD | (SEQ ID NO. 90) |
| HGSSAHP | (SEQ ID NO. 64) | NSPNPSI | (SEQ ID NO. 91) |
| SYGPMTN | (SEQ ID NO. 65) | TQMPKQQ | (SEQ ID NO. 92) |
| PTETPQM | (SEQ ID NO. 66) | SPMQPRL | (SEQ ID NO. 93) |
| HAQLASL | (SEQ ID NO. 67) | FTANLRA | (SEQ ID NO. 94) |
| LHQNQKS | (SEQ ID NO. 68) | FNSMSNSRGYAL | (SEQ ID NO. 95) |
| HPSDTIL | (SEQ ID NO. 69) | LFLPPTPPPEPL | (SEQ ID NO. 96) |
| TTAAPQM | (SEQ ID NO. 70) | QAVKASHATMYL | (SEQ ID NO. 97) |
| SSNLPFA | (SEQ ID NO. 71) | TPASIMRMPLPG | (SEQ ID NO. 98) |
| TGPEQGL | (SEQ ID NO. 72) | ETQPSAMGGSSL | (SEQ ID NO. 99) |
| NVASTRI | (SEQ ID NO. 73) | VAKQVTTPGSST | (SEQ ID NO. 100) |
| SNVHHPS | (SEQ ID NO. 74) | TYNDIQAPVPSL | (SEQ ID NO. 101) |
| TLAHRGE | (SEQ ID NO. 75) | STSWPPQPHLSP | (SEQ ID NO. 102) |
| NAPHRTL | (SEQ ID NO. 76) | TYPLQTAASRLQ | (SEQ ID NO. 103) |
| TTTTPFA | (SEQ ID NO. 77) | SYDLIPPRSGLA | (SEQ ID NO. 104) |
| TTQMQRM | (SEQ ID NO. 78) | NTTQTLRHVSLA | (SEQ ID NO. 105) |
| STMTRAT | (SEQ ID NO. 79) | TIVGPIIGGTAG | (SEQ ID NO. 106) |
| SWNTSPL | (SEQ ID NO. 80) | TSGFDRALSPSL | (SEQ ID NO. 107) |
| PDSQTGN | (SEQ ID NO. 81) | DLHNHQTTSLRY | (SEQ ID NO. 108) |
| PSPPTNQ | (SEQ ID NO. 82) | RXXVDXPPPAL | (SEQ ID NO. 109) |
| IKPELMH | (SEQ ID NO. 83) | SALEQSTERPPS | (SEQ ID NO. 110) |
| | | SNSTMNALAPA | (SEQ ID NO. 111) |

*FIG. 1B*

| | | | |
|---|---|---|---|
| QSTDLQA | (SEQ ID NO. 112) | LPTSTLT | (SEQ ID NO. 139) |
| AISITGS | (SEQ ID NO. 113) | LQDCLRN | (SEQ ID NO. 140) |
| ALGXIPXTAHQW | (SEQ ID NO. 114) | LSTPGMQ | (SEQ ID NO. 141) |
| ARSIQPF | (SEQ ID NO. 115) | LTPDAIF | (SEQ ID NO. 142) |
| ATVILTD | (SEQ ID NO. 116) | MVQGTSE | (SEQ ID NO. 143) |
| DAHPTRT | (SEQ ID NO. 117) | NLKVQQR | (SEQ ID NO. 144) |
| DPNTTSH | (SEQ ID NO. 118) | NSAPHVT | (SEQ ID NO. 145) |
| EPAPPRK | (SEQ ID NO. 119) | NTNPFQP | (SEQ ID NO. 146) |
| FLPLLTL | (SEQ ID NO. 120) | NVTMVLL | (SEQ ID NO. 147) |
| FQLIPTG | (SEQ ID NO. 121) | NXKTSQX | (SEQ ID NO. 148) |
| GAFFTAY | (SEQ ID NO. 122) | PGKHGQA | (SEQ ID NO. 149) |
| GHPQLPL | (SEQ ID NO. 123) | PITPVXA | (SEQ ID NO. 150) |
| GPSXLWX | (SEQ ID NO. 124) | PPIIDLE | (SEQ ID NO. 151) |
| GVPFATP | (SEQ ID NO. 125) | PPSPLTP | (SEQ ID NO. 152) |
| HNLRFAH | (SEQ ID NO. 126) | PQXGIXX | (SEQ ID NO. 153) |
| HRHPPGL | (SEQ ID NO. 127) | PTLAGAS | (SEQ ID NO. 154) |
| HTDQTSD | (SEQ ID NO. 128) | PTLFKEH | (SEQ ID NO. 155) |
| HXGPRLEXASDF | (SEQ ID NO. 129) | PYLSDKA | (SEQ ID NO. 156) |
| IPLIKGMHPPD | (SEQ ID NO. 130) | QDTAPLT | (SEQ ID NO. 157) |
| IPTTRQT | (SEQ ID NO. 131) | QNQKSTT | (SEQ ID NO. 158) |
| KASHLVP | (SEQ ID NO. 132) | QPGHLDI | (SEQ ID NO. 159) |
| KDAKKIT | (SEQ ID NO. 133) | QSDMHWR | (SEQ ID NO. 160) |
| KDPSWPSQAQTP | (SEQ ID NO. 134) | QSEPHPK | (SEQ ID NO. 161) |
| KPXLPTX | (SEQ ID NO. 135) | RAGESHR | (SEQ ID NO. 162) |
| LKEFQQI | (SEQ ID NO. 136) | RDAYLTP | (SEQ ID NO. 163) |
| LLLSPPP | (SEQ ID NO. 137) | RLSLPMQ | (SEQ ID NO. 164) |
| LPKHTLT | (SEQ ID NO. 138) | RMATPNA | (SEQ ID NO. 165) |
| | | SASATWT | (SEQ ID NO. 166) |
| | | SGPADAD | (SEQ ID NO. 167) |

*FIG. 2A*

| | | | |
|---|---|---|---|
| SIIPPRQ | (SEQ ID NO. 168) | XALPWKS | (SEQ ID NO. 194) |
| SKNTAFG | (SEQ ID NO. 169) | XDSXSXX | (SEQ ID NO. 195) |
| SLSTXAN | (SEQ ID NO. 170) | XPTVDNH | (SEQ ID NO. 196) |
| SMWGNLH | (SEQ ID NO. 171) | XPXXVFX | (SEQ ID NO. 197) |
| SNHLIQY | (SEQ ID NO. 172) | YADSVQM | (SEQ ID NO. 198) |
| SRAWSWP | (SEQ ID NO. 173) | YPAPKPY | (SEQ ID NO. 199) |
| SSLLPRS | (SEQ ID NO. 174) | YSIXVMGYYTPY | (SEQ ID NO. 200) |
| SVSLVSL | (SEQ ID NO. 175) | YTKTSQY | (SEQ ID NO. 201) |
| SXTLSPY | (SEQ ID NO. 176) | | |
| TAPLISI | (SEQ ID NO. 177) | | |
| TIQSRYT | (SEQ ID NO. 178) | | |
| TKSSMPT | (SEQ ID NO. 179) | | |
| TKTTWQT | (SEQ ID NO. 180) | | |
| TLFYTKX | (SEQ ID NO. 181) | | |
| TQRLTTH | (SEQ ID NO. 182) | | |
| TRESGEQ | (SEQ ID NO. 183) | | |
| TSLVPDK | (SEQ ID NO. 184) | | |
| TTMAYVA | (SEQ ID NO. 185) | | |
| TVPMRSL | (SEQ ID NO. 186) | | |
| VDRNQSLRSFXT | (SEQ ID NO. 187) | | |
| VGQGNTS | (SEQ ID NO. 188) | | |
| VLPMYSH | (SEQ ID NO. 189) | | |
| WLRPXLH | (SEQ ID NO. 190) | | |
| WQLARPK | (SEQ ID NO. 191) | | |
| WQTXLTD | (SEQ ID NO. 192) | | |
| WSNKPLSPNDLR | (SEQ ID NO. 193) | | |

FIG. 2B

| | | | |
|---|---|---|---|
| ADKTKNY | (SEQ ID NO. 202) | NSSPFATMPNAL | (SEQ ID NO. 227) |
| QYHGPLP | (SEQ ID NO. 203) | TCNAMSSLCDPP | (SEQ ID NO. 228) |
| TPPMGRH | (SEQ ID NO. 204) | SPLPPLVGSLLK | (SEQ ID NO. 229) |
| HPTAQTL | (SEQ ID NO. 205) | FPTKHTLSTTIY | (SEQ ID NO. 230) |
| SDESMNM | (SEQ ID NO. 206) | HGPRPPGMTLPI | (SEQ ID NO. 231) |
| SHFSGNR | (SEQ ID NO. 207) | SPLLTYKQQAL | (SEQ ID NO. 232) |
| DHNQTNR | (SEQ ID NO. 208) | KLPYPFPPEAMV | (SEQ ID NO. 233) |
| LHTHSNT | (SEQ ID NO. 209) | HPFLPPSKTAPP | (SEQ ID NO. 234) |
| NGNFDSA | (SEQ ID NO. 210) | WTXCVECTFATP | (SEQ ID NO. 235) |
| RPLMSTQ | (SEQ ID NO. 211) | GAKHYARVAAEF | (SEQ ID NO. 236) |
| VNDPTTI | (SEQ ID NO. 212) | GIMQSTPPANQQ | (SEQ ID NO. 237) |
| TGNSSQQ | (SEQ ID NO. 213) | YGTQQQDRLHKP | (SEQ ID NO. 238) |
| KSTLYHT | (SEQ ID NO. 214) | VDEFLHAMPLNA | (SEQ ID NO. 239) |
| KAAHDEG | (SEQ ID NO. 215) | HMPHPATVHLLW | (SEQ ID NO. 240) |
| WHTGPSE | (SEQ ID NO. 216) | RAATAELPGGRV | (SEQ ID NO. 241) |
| ITQERNQ | (SEQ ID NO. 217) | LIEPYTRSANSF | (SEQ ID NO. 242) |
| GNDQVSP | (SEQ ID NO. 218) | DVDQLRSAVWSR | (SEQ ID NO. 243) |
| LTDSFLG | (SEQ ID NO. 219) | LSVTTNT | (SEQ ID NO. 244) |
| PYTWHLE | (SEQ ID NO. 220) | DSLFKWT | (SEQ ID NO. 245) |
| ATDNTLQ | (SEQ ID NO. 221) | FETKAND | (SEQ ID NO. 246) |
| PVSMIST | (SEQ ID NO. 222) | NVNNHIH | (SEQ ID NO. 247) |
| LNKTSPN | (SEQ ID NO. 223) | QPAKGVL | (SEQ ID NO. 248) |
| SSYQINTTPALP | (SEQ ID NO. 224) | DYAHGNT | (SEQ ID NO. 249) |
| LPLQPLMPPLNQ | (SEQ ID NO. 225) | SRSELPL | (SEQ ID NO. 250) |
| FYFPQNLVYQAG | (SEQ ID NO. 226) | ADRLRPT | (SEQ ID NO. 251) |
| | | HSPQMQS | (SEQ ID NO. 252) |
| | | NLARDGT | (SEQ ID NO. 253) |

*FIG. 3A*

| | | | |
|---|---|---|---|
| TGNKSSM | (SEQ ID NO. 254) | VPINSSV | (SEQ ID NO. 278) |
| TKDAWPS | (SEQ ID NO. 255) | KSNNTGY | (SEQ ID NO. 279) |
| SPALVNS | (SEQ ID NO. 256) | LWNAKLA | (SEQ ID NO. 280) |
| VNSDNAY | (SEQ ID NO. 257) | QMTQTQS | (SEQ ID NO. 281) |
| TAEVTRG | (SEQ ID NO. 258) | TSGPHPL | (SEQ ID NO. 282) |
| TNKIPPL | (SEQ ID NO. 259) | NEALGHL | (SEQ ID NO. 283) |
| TNPNHIM | (SEQ ID NO. 260) | SGLSKLN | (SEQ ID NO. 284) |
| SSATSIT | (SEQ ID NO. 261) | KHADSTS | (SEQ ID NO. 285) |
| QPLKTKQ | (SEQ ID NO. 262) | STSQHNV | (SEQ ID NO. 286) |
| IESRSMQ | (SEQ ID NO. 263) | TTQTNKD | (SEQ ID NO. 287) |
| SFKSMTF | (SEQ ID NO. 264) | NTAATGT | (SEQ ID NO. 288) |
| HSLMMPN | (SEQ ID NO. 265) | PATNPNH | (SEQ ID NO. 289) |
| TKSPTAI | (SEQ ID NO. 266) | LAETHSS | (SEQ ID NO. 290) |
| LASENMN | (SEQ ID NO. 267) | HTDTSPQ | (SEQ ID NO. 291) |
| PPHSHQL | (SEQ ID NO. 268) | SPLYHDR | (SEQ ID NO. 292) |
| QVNYTSV | (SEQ ID NO. 269) | LKYLERD | (SEQ ID NO. 293) |
| KSPEYPF | (SEQ ID NO. 270) | LSEAPGI | (SEQ ID NO. 294) |
| KAPHQKA | (SEQ ID NO. 271) | ERQNNMN | (SEQ ID NO. 295) |
| TRSPSYL | (SEQ ID NO. 272) | NAFESLF | (SEQ ID NO. 296) |
| PNPWNAF | (SEQ ID NO. 273) | CYIPTPR | (SEQ ID NO. 297) |
| PSSHSYR | (SEQ ID NO. 274) | NSYNSGL | (SEQ ID NO. 298) |
| KVNMLHD | (SEQ ID NO. 275) | DPQANLT | (SEQ ID NO. 299) |
| TAHAMHL | (SEQ ID NO. 276) | RQANLTQ | (SEQ ID NO. 300) |
| HPGLSNK | (SEQ ID NO. 277) | LDQHSMK | (SEQ ID NO. 301) |
| | | HNMHQAV | (SEQ ID NO. 302) |
| | | LNTLLGT | (SEQ ID NO. 303) |
| | | LLPRLHD | (SEQ ID NO. 304) |

*FIG. 3B*

| | |
|---|---|
| PHHKMQN | (SEQ ID NO. 305) |
| PGEARGE | (SEQ ID NO. 306) |
| GSHSPPQ | (SEQ ID NO. 307) |
| KLQAHPN | (SEQ ID NO. 308) |
| FTMNDIR | (SEQ ID NO. 309) |
| PSTTKHG | (SEQ ID NO. 310) |
| NSTRTFA | (SEQ ID NO. 311) |
| PSHTNVN | (SEQ ID NO. 312) |
| KPTFIRA | (SEQ ID NO. 313) |
| DPRKSAQ | (SEQ ID NO. 314) |
| GLTRHQA | (SEQ ID NO. 315) |
| SASTPRA | (SEQ ID NO. 316) |

*FIG. 3C*

SEQUENCE LISTING

<160> NUMBER OF SEQ ID NOS: 332

<210> SEQ ID NO 1
<211> LENGTH: 7
<212> TYPE: PRT
<213> ORGANISM: Artificial Sequence
<220> FEATURE:
<223> OTHER INFORMATION: binding peptide

<400> SEQUENCE: 1

Lys Thr Pro Ser Pro His Gly
 1               5

<210> SEQ ID NO 2
<211> LENGTH: 7
<212> TYPE: PRT
<213> ORGANISM: Artificial Sequence
<220> FEATURE:
<223> OTHER INFORMATION: binding peptide

<400> SEQUENCE: 2

Pro Asn Thr Thr Arg His Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: binding peptide

<400> SEQUENCE: 3

Gly Lys Met Tyr Leu Lys Ala
 1               5

<210> SEQ ID NO 4
<211> LENGTH: 7
<212> TYPE: PRT
<213> ORGANISM: Artificial Sequence
<220> FEATURE:
<223> OTHER INFORMATION: binding peptide

<400> SEQUENCE: 4

Asn Gln Ser His Met Pro Arg
 1               5

<210> SEQ ID NO 5
<211> LENGTH: 7
<212> TYPE: PRT
<213> ORGANISM: Artificial Sequence
<220> FEATURE:
<223> OTHER INFORMATION: binding peptide

<400> SEQUENCE: 5

Lys Thr Pro Ser Ser Met Glu
 1               5

<210> SEQ ID NO 6
<211> LENGTH: 7
<212> TYPE: PRT
<213> ORGANISM: Artificial Sequence
<220> FEATURE:
<223> OTHER INFORMATION: binding peptide

<400> SEQUENCE: 6

Ile Glu Lys Pro His Ala Asp

<210> SEQ ID NO 7
<211> LENGTH: 7
<212> TYPE: PRT
<213> ORGANISM: Artificial Sequence
<220> FEATURE:
<223> OTHER INFORMATION: binding peptide

<400> SEQUENCE: 7

Pro Thr Tyr His His Gln Thr
1               5

<210> SEQ ID NO 8
<211> LENGTH: 7
<212> TYPE: PRT
<213> ORGANISM: Artificial Sequence
<220> FEATURE:
<223> OTHER INFORMATION: binding peptide

<400> SEQUENCE: 8

Leu Trp Thr Ser Pro Gln Leu
1               5

<210> SEQ ID NO 9
<211> LENGTH: 7
<212> TYPE: PRT
<213> ORGANISM: Artificial Sequence
<220> FEATURE:
<223> OTHER INFORMATION: binding peptide

<400> SEQUENCE: 9

His Ser Leu Asp Gln Arg Ser
1               5

<210> SEQ ID NO 10
<211> LENGTH: 7
<212> TYPE: PRT
<213> ORGANISM: Artificial Sequence
<220> FEATURE:
<223> OTHER INFORMATION: binding peptide

<400> SEQUENCE: 10

Gln Ile Gln Thr Pro Leu Ser
1               5

<210> SEQ ID NO 11
<211> LENGTH: 7
<212> TYPE: PRT
<213> ORGANISM: Artificial Sequence
<220> FEATURE:
<223> OTHER INFORMATION: binding peptide

<400> SEQUENCE: 11

Ser Leu Asn Asn Thr Asn Thr
1               5

<210> SEQ ID NO 12
<211> LENGTH: 7
<212> TYPE: PRT
<213> ORGANISM: Artificial Sequence
<220> FEATURE:
<223> OTHER INFORMATION: binding peptide

<400> SEQUENCE: 12

Val Pro Thr Gly Lys Leu Gln
1               5

```
<210> SEQ ID NO 13
<211> LENGTH: 7
<212> TYPE: PRT
<213> ORGANISM: Artificial Sequence
<220> FEATURE:
<223> OTHER INFORMATION: binding peptide

<400> SEQUENCE: 13

Pro Thr Trp Ser Leu Ala Met
 1               5

<210> SEQ ID NO 14
<211> LENGTH: 7
<212> TYPE: PRT
<213> ORGANISM: Artificial Sequence
<220> FEATURE:
<223> OTHER INFORMATION: binding peptide

<400> SEQUENCE: 14

Leu Gly Thr Pro Gln Gln Thr
 1               5

<210> SEQ ID NO 15
<211> LENGTH: 7
<212> TYPE: PRT
<213> ORGANISM: Artificial Sequence
<220> FEATURE:
<223> OTHER INFORMATION: binding peptide

<400> SEQUENCE: 15

Ser Phe Tyr His Gln Thr Tyr
 1               5

<210> SEQ ID NO 16
<211> LENGTH: 7
<212> TYPE: PRT
<213> ORGANISM: Artificial Sequence
<220> FEATURE:
<223> OTHER INFORMATION: binding peptide

<400> SEQUENCE: 16

Met Met Asn Ser Trp His Lys
 1               5

<210> SEQ ID NO 17
<211> LENGTH: 7
<212> TYPE: PRT
<213> ORGANISM: Artificial Sequence
<220> FEATURE:
<223> OTHER INFORMATION: binding peptide

<400> SEQUENCE: 17

Lys Gln Ser Gln Pro Gln Thr
 1               5

<210> SEQ ID NO 18
<211> LENGTH: 7
<212> TYPE: PRT
<213> ORGANISM: Artificial Sequence
<220> FEATURE:
<223> OTHER INFORMATION: binding peptide

<400> SEQUENCE: 18

Gln Lys His Ser Pro Gly His
 1               5

<210> SEQ ID NO 19
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 19

Thr Ser Gly Ser Met His Ser
1               5

<210> SEQ ID NO 20
<211> LENGTH: 7
<212> TYPE: PRT
<213> ORGANISM: Artificial Sequence
<220> FEATURE:
<223> OTHER INFORMATION: binding peptide

<400> SEQUENCE: 20

Val Leu Arg Pro Ala Ala Leu
1               5

<210> SEQ ID NO 21
<211> LENGTH: 7
<212> TYPE: PRT
<213> ORGANISM: Artificial Sequence
<220> FEATURE:
<223> OTHER INFORMATION: binding peptide

<400> SEQUENCE: 21

Ser Pro Met Asp Glu Tyr Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: binding peptide

<400> SEQUENCE: 22

Leu Lys Ser Thr Arg Pro Thr
1               5

<210> SEQ ID NO 23
<211> LENGTH: 7
<212> TYPE: PRT
<213> ORGANISM: Artificial Sequence
<220> FEATURE:
<223> OTHER INFORMATION: binding peptide

<400> SEQUENCE: 23

Asp Ser Arg Leu Ser Arg Ser
1               5

<210> SEQ ID NO 24
<211> LENGTH: 7
<212> TYPE: PRT
<213> ORGANISM: Artificial Sequence
<220> FEATURE:
<223> OTHER INFORMATION: binding peptide

<400> SEQUENCE: 24

Thr Asn Asn Thr Ser Pro Thr
1               5

<210> SEQ ID NO 25
<211> LENGTH: 7
<212> TYPE: PRT
```

```
<213> ORGANISM: Artificial Sequence
<220> FEATURE:
<223> OTHER INFORMATION: binding peptide

<400> SEQUENCE: 25

Gln Thr Gln Pro Pro Gly Ser
 1               5

<210> SEQ ID NO 26
<211> LENGTH: 7
<212> TYPE: PRT
<213> ORGANISM: Artificial Sequence
<220> FEATURE:
<223> OTHER INFORMATION: binding peptide

<400> SEQUENCE: 26

Leu Lys Asn Val Pro Phe Arg
 1               5

<210> SEQ ID NO 27
<211> LENGTH: 7
<212> TYPE: PRT
<213> ORGANISM: Artificial Sequence
<220> FEATURE:
<223> OTHER INFORMATION: binding peptide

<400> SEQUENCE: 27

His Asn Tyr Thr Leu Gln Lys
 1               5

<210> SEQ ID NO 28
<211> LENGTH: 7
<212> TYPE: PRT
<213> ORGANISM: Artificial Sequence
<220> FEATURE:
<223> OTHER INFORMATION: binding peptide

<400> SEQUENCE: 28

Lys Phe Met His Thr Thr Ala
 1               5

<210> SEQ ID NO 29
<211> LENGTH: 7
<212> TYPE: PRT
<213> ORGANISM: Artificial Sequence
<220> FEATURE:
<223> OTHER INFORMATION: binding peptide

<400> SEQUENCE: 29

Lys Thr Ser Ile Gly His Trp
 1               5

<210> SEQ ID NO 30
<211> LENGTH: 7
<212> TYPE: PRT
<213> ORGANISM: Artificial Sequence
<220> FEATURE:
<223> OTHER INFORMATION: binding peptide

<400> SEQUENCE: 30

Leu Pro Ala Lys Pro Leu Ala
 1               5

<210> SEQ ID NO 31
<211> LENGTH: 7
<212> TYPE: PRT
<213> ORGANISM: Artificial Sequence
<220> FEATURE:
```

<223> OTHER INFORMATION: binding peptide

<400> SEQUENCE: 31

Leu Asn Ser Ser Ser Lys Ser
 1               5

<210> SEQ ID NO 32
<211> LENGTH: 7
<212> TYPE: PRT
<213> ORGANISM: Artificial Sequence
<220> FEATURE:
<223> OTHER INFORMATION: binding peptide

<400> SEQUENCE: 32

Asn Lys Ser Asn Ala Thr Val
 1               5

<210> SEQ ID NO 33
<211> LENGTH: 7
<212> TYPE: PRT
<213> ORGANISM: Artificial Sequence
<220> FEATURE:
<223> OTHER INFORMATION: binding peptide

<400> SEQUENCE: 33

Ala Leu Asn Pro Leu His Thr
 1               5

<210> SEQ ID NO 34
<211> LENGTH: 7
<212> TYPE: PRT
<213> ORGANISM: Artificial Sequence
<220> FEATURE:
<223> OTHER INFORMATION: binding peptide

<400> SEQUENCE: 34

Asp Thr His Thr Gln Lys His
 1               5

<210> SEQ ID NO 35
<211> LENGTH: 7
<212> TYPE: PRT
<213> ORGANISM: Artificial Sequence
<220> FEATURE:
<223> OTHER INFORMATION: binding peptide

<400> SEQUENCE: 35

Thr Ala Gln Ile His Ser Val
 1               5

<210> SEQ ID NO 36
<211> LENGTH: 7
<212> TYPE: PRT
<213> ORGANISM: Artificial Sequence
<220> FEATURE:
<223> OTHER INFORMATION: binding peptide

<400> SEQUENCE: 36

Thr Met Ala Pro Ala Lys Asn
 1               5

<210> SEQ ID NO 37
<211> LENGTH: 7
<212> TYPE: PRT
<213> ORGANISM: Artificial Sequence
<220> FEATURE:
<223> OTHER INFORMATION: binding peptide

```
<400> SEQUENCE: 37

Ser His Leu Asp Lys Arg Leu
 1               5

<210> SEQ ID NO 38
<211> LENGTH: 7
<212> TYPE: PRT
<213> ORGANISM: Artificial Sequence
<220> FEATURE:
<223> OTHER INFORMATION: binding peptide

<400> SEQUENCE: 38

Thr Asn Trp Asp Ala Pro Thr
 1               5

<210> SEQ ID NO 39
<211> LENGTH: 7
<212> TYPE: PRT
<213> ORGANISM: Artificial Sequence
<220> FEATURE:
<223> OTHER INFORMATION: binding peptide

<400> SEQUENCE: 39

Thr Met Ser Arg Val Asn Gln
 1               5

<210> SEQ ID NO 40
<211> LENGTH: 7
<212> TYPE: PRT
<213> ORGANISM: Artificial Sequence
<220> FEATURE:
<223> OTHER INFORMATION: binding peptide

<400> SEQUENCE: 40

Thr Thr Thr Asn Lys Pro Leu
 1               5

<210> SEQ ID NO 41
<211> LENGTH: 7
<212> TYPE: PRT
<213> ORGANISM: Artificial Sequence
<220> FEATURE:
<223> OTHER INFORMATION: binding peptide

<400> SEQUENCE: 41

Leu Thr Gln Asn Phe His Ser
 1               5

<210> SEQ ID NO 42
<211> LENGTH: 7
<212> TYPE: PRT
<213> ORGANISM: Artificial Sequence
<220> FEATURE:
<223> OTHER INFORMATION: binding peptide

<400> SEQUENCE: 42

Asn Pro Thr Gln Leu Gln Asn
 1               5

<210> SEQ ID NO 43
<211> LENGTH: 7
<212> TYPE: PRT
<213> ORGANISM: Artificial Sequence
<220> FEATURE:
<223> OTHER INFORMATION: binding peptide

<400> SEQUENCE: 43
```

```
Ser Pro Thr Ser Thr Asn Ser
1               5

<210> SEQ ID NO 44
<211> LENGTH: 7
<212> TYPE: PRT
<213> ORGANISM: Artificial Sequence
<220> FEATURE:
<223> OTHER INFORMATION: binding peptide

<400> SEQUENCE: 44

Pro Gly Ser Asn Ala Thr Gln
1               5

<210> SEQ ID NO 45
<211> LENGTH: 7
<212> TYPE: PRT
<213> ORGANISM: Artificial Sequence
<220> FEATURE:
<223> OTHER INFORMATION: binding peptide

<400> SEQUENCE: 45

Ser Gln Asp Thr Pro Met Tyr
1               5

<210> SEQ ID NO 46
<211> LENGTH: 7
<212> TYPE: PRT
<213> ORGANISM: Artificial Sequence
<220> FEATURE:
<223> OTHER INFORMATION: binding peptide

<400> SEQUENCE: 46

Thr Asp Pro Ser Met Met Asn
1               5

<210> SEQ ID NO 47
<211> LENGTH: 7
<212> TYPE: PRT
<213> ORGANISM: Artificial Sequence
<220> FEATURE:
<223> OTHER INFORMATION: binding peptide

<400> SEQUENCE: 47

Gly Gln Ala Asp Arg Leu Gln
1               5

<210> SEQ ID NO 48
<211> LENGTH: 7
<212> TYPE: PRT
<213> ORGANISM: Artificial Sequence
<220> FEATURE:
<223> OTHER INFORMATION: binding peptide

<400> SEQUENCE: 48

Thr Pro Gln Arg Leu Leu Thr
1               5

<210> SEQ ID NO 49
<211> LENGTH: 7
<212> TYPE: PRT
<213> ORGANISM: Artificial Sequence
<220> FEATURE:
<223> OTHER INFORMATION: binding peptide

<400> SEQUENCE: 49

Gln Trp Thr Asp Pro Met Lys
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: binding peptide

<400> SEQUENCE: 50

Ala Lys Thr Asn Leu Lys Asp
 1               5

<210> SEQ ID NO 51
<211> LENGTH: 7
<212> TYPE: PRT
<213> ORGANISM: Artificial Sequence
<220> FEATURE:
<223> OTHER INFORMATION: binding peptide

<400> SEQUENCE: 51

Glu Val Thr Thr Val Arg Asn
 1               5

<210> SEQ ID NO 52
<211> LENGTH: 7
<212> TYPE: PRT
<213> ORGANISM: Artificial Sequence
<220> FEATURE:
<223> OTHER INFORMATION: binding peptide

<400> SEQUENCE: 52

Leu Asn Asn Tyr Arg Asn Met
 1               5

<210> SEQ ID NO 53
<211> LENGTH: 7
<212> TYPE: PRT
<213> ORGANISM: Artificial Sequence
<220> FEATURE:
<223> OTHER INFORMATION: binding peptide

<400> SEQUENCE: 53

Ser Gln Met Ser Pro Leu His
 1               5

<210> SEQ ID NO 54
<211> LENGTH: 7
<212> TYPE: PRT
<213> ORGANISM: Artificial Sequence
<220> FEATURE:
<223> OTHER INFORMATION: binding peptide

<400> SEQUENCE: 54

Ser Ala Arg Ser Leu Pro Phe
 1               5

<210> SEQ ID NO 55
<211> LENGTH: 7
<212> TYPE: PRT
<213> ORGANISM: Artificial Sequence
<220> FEATURE:
<223> OTHER INFORMATION: binding peptide

<400> SEQUENCE: 55

Pro Thr His Leu Ala Asn Met
 1               5
```

```
<210> SEQ ID NO 56
<211> LENGTH: 7
<212> TYPE: PRT
<213> ORGANISM: Artificial Sequence
<220> FEATURE:
<223> OTHER INFORMATION: binding peptide

<400> SEQUENCE: 56

Thr Gln Lys Asp Asp Arg Gln
1               5

<210> SEQ ID NO 57
<211> LENGTH: 7
<212> TYPE: PRT
<213> ORGANISM: Artificial Sequence
<220> FEATURE:
<223> OTHER INFORMATION: binding peptide

<400> SEQUENCE: 57

Thr Asp Phe His Gln Gly Thr
1               5

<210> SEQ ID NO 58
<211> LENGTH: 7
<212> TYPE: PRT
<213> ORGANISM: Artificial Sequence
<220> FEATURE:
<223> OTHER INFORMATION: binding peptide

<400> SEQUENCE: 58

Thr Tyr Glu Ala Pro Arg Thr
1               5

<210> SEQ ID NO 59
<211> LENGTH: 7
<212> TYPE: PRT
<213> ORGANISM: Artificial Sequence
<220> FEATURE:
<223> OTHER INFORMATION: binding peptide

<400> SEQUENCE: 59

Leu Gln Ile Asn Ala Gln Thr
1               5

<210> SEQ ID NO 60
<211> LENGTH: 7
<212> TYPE: PRT
<213> ORGANISM: Artificial Sequence
<220> FEATURE:
<223> OTHER INFORMATION: binding peptide

<400> SEQUENCE: 60

His Val Trp Ser Gln Ala Trp
1               5

<210> SEQ ID NO 61
<211> LENGTH: 7
<212> TYPE: PRT
<213> ORGANISM: Artificial Sequence
<220> FEATURE:
<223> OTHER INFORMATION: binding peptide

<400> SEQUENCE: 61

His Gln Gly Pro Leu Arg Thr
1               5

<210> SEQ ID NO 62
<211> LENGTH: 7
```

```
<212> TYPE: PRT
<213> ORGANISM: Artificial Sequence
<220> FEATURE:
<223> OTHER INFORMATION: binding peptide

<400> SEQUENCE: 62

Thr Gln Asn Pro Thr His Ser
1               5

<210> SEQ ID NO 63
<211> LENGTH: 7
<212> TYPE: PRT
<213> ORGANISM: Artificial Sequence
<220> FEATURE:
<223> OTHER INFORMATION: binding peptide

<400> SEQUENCE: 63

Glu Asn Ser Phe Ala Gly Gly
1               5

<210> SEQ ID NO 64
<211> LENGTH: 7
<212> TYPE: PRT
<213> ORGANISM: Artificial Sequence
<220> FEATURE:
<223> OTHER INFORMATION: binding peptide

<400> SEQUENCE: 64

His Gly Ser Ser Ala His Pro
1               5

<210> SEQ ID NO 65
<211> LENGTH: 7
<212> TYPE: PRT
<213> ORGANISM: Artificial Sequence
<220> FEATURE:
<223> OTHER INFORMATION: binding peptide

<400> SEQUENCE: 65

Ser Tyr Gly Pro Met Thr Asn
1               5

<210> SEQ ID NO 66
<211> LENGTH: 7
<212> TYPE: PRT
<213> ORGANISM: Artificial Sequence
<220> FEATURE:
<223> OTHER INFORMATION: binding peptide

<400> SEQUENCE: 66

Pro Thr Glu Thr Pro Gln Met
1               5

<210> SEQ ID NO 67
<211> LENGTH: 7
<212> TYPE: PRT
<213> ORGANISM: Artificial Sequence
<220> FEATURE:
<223> OTHER INFORMATION: binding peptide

<400> SEQUENCE: 67

His Ala Gln Leu Ala Ser Leu
1               5

<210> SEQ ID NO 68
<211> LENGTH: 7
<212> TYPE: PRT
<213> ORGANISM: Artificial Sequence
```

<220> FEATURE:
<223> OTHER INFORMATION: binding peptide

<400> SEQUENCE: 68

Leu His Gln Asn Gln Lys Ser
1               5

<210> SEQ ID NO 69
<211> LENGTH: 7
<212> TYPE: PRT
<213> ORGANISM: Artificial Sequence
<220> FEATURE:
<223> OTHER INFORMATION: binding peptide

<400> SEQUENCE: 69

His Pro Ser Asp Thr Ile Leu
1               5

<210> SEQ ID NO 70
<211> LENGTH: 7
<212> TYPE: PRT
<213> ORGANISM: Artificial Sequence
<220> FEATURE:
<223> OTHER INFORMATION: binding peptide

<400> SEQUENCE: 70

Thr Thr Ala Ala Pro Gln Met
1               5

<210> SEQ ID NO 71
<211> LENGTH: 7
<212> TYPE: PRT
<213> ORGANISM: Artificial Sequence
<220> FEATURE:
<223> OTHER INFORMATION: binding peptide

<400> SEQUENCE: 71

Ser Ser Asn Leu Pro Phe Ala
1               5

<210> SEQ ID NO 72
<211> LENGTH: 7
<212> TYPE: PRT
<213> ORGANISM: Artificial Sequence
<220> FEATURE:
<223> OTHER INFORMATION: binding peptide

<400> SEQUENCE: 72

Thr Gly Pro Glu Gln Gly Leu
1               5

<210> SEQ ID NO 73
<211> LENGTH: 7
<212> TYPE: PRT
<213> ORGANISM: Artificial Sequence
<220> FEATURE:
<223> OTHER INFORMATION: binding peptide

<400> SEQUENCE: 73

Asn Val Ala Ser Thr Arg Ile
1               5

<210> SEQ ID NO 74
<211> LENGTH: 7
<212> TYPE: PRT
<213> ORGANISM: Artificial Sequence
<220> FEATURE:
<223> OTHER INFORMATION: binding peptide

```
<400> SEQUENCE: 74

Ser Asn Val His His Pro Ser
1               5

<210> SEQ ID NO 75
<211> LENGTH: 7
<212> TYPE: PRT
<213> ORGANISM: Artificial Sequence
<220> FEATURE:
<223> OTHER INFORMATION: binding peptide

<400> SEQUENCE: 75

Thr Leu Ala His Arg Gly Glu
1               5

<210> SEQ ID NO 76
<211> LENGTH: 7
<212> TYPE: PRT
<213> ORGANISM: Artificial Sequence
<220> FEATURE:
<223> OTHER INFORMATION: binding peptide

<400> SEQUENCE: 76

Asn Ala Pro His Arg Thr Leu
1               5

<210> SEQ ID NO 77
<211> LENGTH: 7
<212> TYPE: PRT
<213> ORGANISM: Artificial Sequence
<220> FEATURE:
<223> OTHER INFORMATION: binding peptide

<400> SEQUENCE: 77

Thr Thr Thr Thr Pro Phe Ala
1               5

<210> SEQ ID NO 78
<211> LENGTH: 7
<212> TYPE: PRT
<213> ORGANISM: Artificial Sequence
<220> FEATURE:
<223> OTHER INFORMATION: binding peptide

<400> SEQUENCE: 78

Thr Thr Gln Met Gln Arg Met
1               5

<210> SEQ ID NO 79
<211> LENGTH: 7
<212> TYPE: PRT
<213> ORGANISM: Artificial Sequence
<220> FEATURE:
<223> OTHER INFORMATION: binding peptide

<400> SEQUENCE: 79

Ser Thr Met Thr Arg Ala Thr
1               5

<210> SEQ ID NO 80
<211> LENGTH: 7
<212> TYPE: PRT
<213> ORGANISM: Artificial Sequence
<220> FEATURE:
<223> OTHER INFORMATION: binding peptide

<400> SEQUENCE: 80
```

Ser Trp Asn Thr Ser Pro Leu
1               5

<210> SEQ ID NO 81
<211> LENGTH: 7
<212> TYPE: PRT
<213> ORGANISM: Artificial Sequence
<220> FEATURE:
<223> OTHER INFORMATION: binding peptide

<400> SEQUENCE: 81

Pro Asp Ser Gln Thr Gly Asn
1               5

<210> SEQ ID NO 82
<211> LENGTH: 7
<212> TYPE: PRT
<213> ORGANISM: Artificial Sequence
<220> FEATURE:
<223> OTHER INFORMATION: binding peptide

<400> SEQUENCE: 82

Pro Ser Pro Pro Thr Asn Gln
1               5

<210> SEQ ID NO 83
<211> LENGTH: 7
<212> TYPE: PRT
<213> ORGANISM: Artificial Sequence
<220> FEATURE:
<223> OTHER INFORMATION: binding peptide

<400> SEQUENCE: 83

Ile Lys Pro Glu Leu Met His
1               5

<210> SEQ ID NO 84
<211> LENGTH: 7
<212> TYPE: PRT
<213> ORGANISM: Artificial Sequence
<220> FEATURE:
<223> OTHER INFORMATION: binding peptide

<400> SEQUENCE: 84

Asn Glu Ile Asn Ala Gln Ser
1               5

<210> SEQ ID NO 85
<211> LENGTH: 7
<212> TYPE: PRT
<213> ORGANISM: Artificial Sequence
<220> FEATURE:
<223> OTHER INFORMATION: binding peptide

<400> SEQUENCE: 85

Pro Leu Thr Ser Thr Gln Pro
1               5

<210> SEQ ID NO 86
<211> LENGTH: 7
<212> TYPE: PRT
<213> ORGANISM: Artificial Sequence
<220> FEATURE:
<223> OTHER INFORMATION: binding peptide

<400> SEQUENCE: 86

Pro Pro Asn Ser Ser Ser Ser

<210> SEQ ID NO 87
<211> LENGTH: 7
<212> TYPE: PRT
<213> ORGANISM: Artificial Sequence
<220> FEATURE:
<223> OTHER INFORMATION: binding peptide

<400> SEQUENCE: 87

His Val Ser Asp Leu Ala Gly
1               5

<210> SEQ ID NO 88
<211> LENGTH: 7
<212> TYPE: PRT
<213> ORGANISM: Artificial Sequence
<220> FEATURE:
<223> OTHER INFORMATION: binding peptide

<400> SEQUENCE: 88

Thr Leu Ser Arg Thr Thr Ala
1               5

<210> SEQ ID NO 89
<211> LENGTH: 7
<212> TYPE: PRT
<213> ORGANISM: Artificial Sequence
<220> FEATURE:
<223> OTHER INFORMATION: binding peptide

<400> SEQUENCE: 89

Ile Asn Lys Thr Met Ala Glu
1               5

<210> SEQ ID NO 90
<211> LENGTH: 7
<212> TYPE: PRT
<213> ORGANISM: Artificial Sequence
<220> FEATURE:
<223> OTHER INFORMATION: binding peptide

<400> SEQUENCE: 90

His Leu Arg Ser Thr Thr Asp
1               5

<210> SEQ ID NO 91
<211> LENGTH: 7
<212> TYPE: PRT
<213> ORGANISM: Artificial Sequence
<220> FEATURE:
<223> OTHER INFORMATION: binding peptide

<400> SEQUENCE: 91

Asn Ser Pro Asn Pro Ser Ile
1               5

<210> SEQ ID NO 92
<211> LENGTH: 7
<212> TYPE: PRT
<213> ORGANISM: Artificial Sequence
<220> FEATURE:
<223> OTHER INFORMATION: binding peptide

<400> SEQUENCE: 92

Thr Gln Met Pro Lys Gln Gln
1               5

```
<210> SEQ ID NO 93
<211> LENGTH: 7
<212> TYPE: PRT
<213> ORGANISM: Artificial Sequence
<220> FEATURE:
<223> OTHER INFORMATION: binding peptide

<400> SEQUENCE: 93

Ser Pro Met Gln Pro Arg Leu
 1               5

<210> SEQ ID NO 94
<211> LENGTH: 7
<212> TYPE: PRT
<213> ORGANISM: Artificial Sequence
<220> FEATURE:
<223> OTHER INFORMATION: binding peptide

<400> SEQUENCE: 94

Phe Thr Ala Asn Leu Arg Ala
 1               5

<210> SEQ ID NO 95
<211> LENGTH: 12
<212> TYPE: PRT
<213> ORGANISM: Artificial Sequence
<220> FEATURE:
<223> OTHER INFORMATION: binding peptide

<400> SEQUENCE: 95

Phe Asn Ser Met Ser Asn Ser Arg Gly Tyr Ala Leu
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: binding peptide

<400> SEQUENCE: 96

Leu Phe Leu Pro Pro Thr Pro Pro Glu Pro Leu
 1               5                  10

<210> SEQ ID NO 97
<211> LENGTH: 12
<212> TYPE: PRT
<213> ORGANISM: Artificial Sequence
<220> FEATURE:
<223> OTHER INFORMATION: binding peptide

<400> SEQUENCE: 97

Gln Ala Val Lys Ala Ser His Ala Thr Met Tyr Leu
 1               5                  10

<210> SEQ ID NO 98
<211> LENGTH: 12
<212> TYPE: PRT
<213> ORGANISM: Artificial Sequence
<220> FEATURE:
<223> OTHER INFORMATION: binding peptide

<400> SEQUENCE: 98

Thr Pro Ala Ser Ile Met Arg Met Pro Leu Pro Gly
 1               5                  10

<210> SEQ ID NO 99
```

```
<211> LENGTH: 12
<212> TYPE: PRT
<213> ORGANISM: Artificial Sequence
<220> FEATURE:
<223> OTHER INFORMATION: binding peptide

<400> SEQUENCE: 99

Glu Thr Gln Pro Ser Ala Met Gly Gly Ser Ser Leu
1               5                   10

<210> SEQ ID NO 100
<211> LENGTH: 12
<212> TYPE: PRT
<213> ORGANISM: Artificial Sequence
<220> FEATURE:
<223> OTHER INFORMATION: binding peptide

<400> SEQUENCE: 100

Val Ala Lys Gln Val Thr Thr Pro Gly Ser Ser Thr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: binding peptide

<400> SEQUENCE: 101

Thr Tyr Asn Asp Ile Gln Ala Pro Val Pro Ser Leu
1               5                   10

<210> SEQ ID NO 102
<211> LENGTH: 12
<212> TYPE: PRT
<213> ORGANISM: Artificial Sequence
<220> FEATURE:
<223> OTHER INFORMATION: binding peptide

<400> SEQUENCE: 102

Ser Thr Ser Trp Pro Pro Gln Pro His Leu Ser Pro
1               5                   10

<210> SEQ ID NO 103
<211> LENGTH: 12
<212> TYPE: PRT
<213> ORGANISM: Artificial Sequence
<220> FEATURE:
<223> OTHER INFORMATION: binding peptide

<400> SEQUENCE: 103

Thr Tyr Pro Leu Gln Thr Ala Ala Ser Arg Leu Gln
1               5                   10

<210> SEQ ID NO 104
<211> LENGTH: 12
<212> TYPE: PRT
<213> ORGANISM: Artificial Sequence
<220> FEATURE:
<223> OTHER INFORMATION: binding peptide

<400> SEQUENCE: 104

Ser Tyr Asp Leu Ile Pro Pro Arg Ser Gly Leu Ala
1               5                   10

<210> SEQ ID NO 105
<211> LENGTH: 12
<212> TYPE: PRT
```

<213> ORGANISM: Artificial Sequence
<220> FEATURE:
<223> OTHER INFORMATION: binding peptide

<400> SEQUENCE: 105

Asn Thr Thr Gln Thr Leu Arg His Val Ser Leu Ala
1               5                   10

<210> SEQ ID NO 106
<211> LENGTH: 12
<212> TYPE: PRT
<213> ORGANISM: Artificial Sequence
<220> FEATURE:
<223> OTHER INFORMATION: binding peptide

<400> SEQUENCE: 106

Thr Ile Val Gly Pro Ile Ile Gly Gly Thr Ala Gly
1               5                   10

<210> SEQ ID NO 107
<211> LENGTH: 12
<212> TYPE: PRT
<213> ORGANISM: Artificial Sequence
<220> FEATURE:
<223> OTHER INFORMATION: binding peptide

<400> SEQUENCE: 107

Thr Ser Gly Phe Asp Arg Ala Leu Ser Pro Ser Leu
1               5                   10

<210> SEQ ID NO 108
<211> LENGTH: 12
<212> TYPE: PRT
<213> ORGANISM: Artificial Sequence
<220> FEATURE:
<223> OTHER INFORMATION: binding peptide

<400> SEQUENCE: 108

Asp Leu His Asn His Gln Thr Thr Ser Leu Arg Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: binding peptide
<221> NAME/KEY: VARIANT
<222> LOCATION: 2, 3, 6
<223> OTHER INFORMATION: Xaa = Any Amino Acid

<400> SEQUENCE: 109

Arg Xaa Xaa Val Asp Xaa Pro Pro Pro Ala Leu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: binding peptide

<400> SEQUENCE: 110

Ser Ala Leu Glu Gln Ser Thr Glu Arg Pro Pro Ser
1               5                   10

<210> SEQ ID NO 111
<211> LENGTH: 11

```
<212> TYPE: PRT
<213> ORGANISM: Artificial Sequence
<220> FEATURE:
<223> OTHER INFORMATION: binding peptide

<400> SEQUENCE: 111

Ser Asn Ser Thr Met Asn Ala Leu Ala Pro Ala
1               5                   10

<210> SEQ ID NO 112
<211> LENGTH: 7
<212> TYPE: PRT
<213> ORGANISM: Artificial Sequence
<220> FEATURE:
<223> OTHER INFORMATION: binding peptide

<400> SEQUENCE: 112

Gln Ser Thr Asp Leu Gln Ala
1               5

<210> SEQ ID NO 113
<211> LENGTH: 7
<212> TYPE: PRT
<213> ORGANISM: Artificial Sequence
<220> FEATURE:
<223> OTHER INFORMATION: binding peptide

<400> SEQUENCE: 113

Ala Ile Ser Ile Thr Gly Ser
1               5

<210> SEQ ID NO 114
<211> LENGTH: 12
<212> TYPE: PRT
<213> ORGANISM: Artificial Sequence
<220> FEATURE:
<223> OTHER INFORMATION: binding peptide
<221> NAME/KEY: VARIANT
<222> LOCATION: 4, 7
<223> OTHER INFORMATION: Xaa = Any Amino Acid

<400> SEQUENCE: 114

Ala Leu Gly Xaa Ile Pro Xaa Thr Ala His Gln Trp
1               5                   10

<210> SEQ ID NO 115
<211> LENGTH: 7
<212> TYPE: PRT
<213> ORGANISM: Artificial Sequence
<220> FEATURE:
<223> OTHER INFORMATION: binding peptide

<400> SEQUENCE: 115

Ala Arg Ser Ile Gln Pro Phe
1               5

<210> SEQ ID NO 116
<211> LENGTH: 7
<212> TYPE: PRT
<213> ORGANISM: Artificial Sequence
<220> FEATURE:
<223> OTHER INFORMATION: binding peptide

<400> SEQUENCE: 116

Ala Thr Val Ile Leu Thr Asp
1               5

<210> SEQ ID NO 117
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 117

Asp Ala His Pro Thr Arg Thr
1               5

<210> SEQ ID NO 118
<211> LENGTH: 7
<212> TYPE: PRT
<213> ORGANISM: Artificial Sequence
<220> FEATURE:
<223> OTHER INFORMATION: binding peptide

<400> SEQUENCE: 118

Asp Pro Asn Thr Thr Ser His
1               5

<210> SEQ ID NO 119
<211> LENGTH: 7
<212> TYPE: PRT
<213> ORGANISM: Artificial Sequence
<220> FEATURE:
<223> OTHER INFORMATION: binding peptide

<400> SEQUENCE: 119

Glu Pro Ala Pro Pro Arg Lys
1               5

<210> SEQ ID NO 120
<211> LENGTH: 7
<212> TYPE: PRT
<213> ORGANISM: Artificial Sequence
<220> FEATURE:
<223> OTHER INFORMATION: binding peptide

<400> SEQUENCE: 120

Phe Leu Pro Leu Leu Thr Leu
1               5

<210> SEQ ID NO 121
<211> LENGTH: 7
<212> TYPE: PRT
<213> ORGANISM: Artificial Sequence
<220> FEATURE:
<223> OTHER INFORMATION: binding peptide

<400> SEQUENCE: 121

Phe Gln Leu Ile Pro Thr Gly
1               5

<210> SEQ ID NO 122
<211> LENGTH: 7
<212> TYPE: PRT
<213> ORGANISM: Artificial Sequence
<220> FEATURE:
<223> OTHER INFORMATION: binding peptide

<400> SEQUENCE: 122

Gly Ala Phe Phe Thr Ala Tyr
1               5

<210> SEQ ID NO 123
<211> LENGTH: 7
<212> TYPE: PRT
```

```
<213> ORGANISM: Artificial Sequence
<220> FEATURE:
<223> OTHER INFORMATION: binding peptide

<400> SEQUENCE: 123

Gly His Pro Gln Leu Pro Leu
1               5

<210> SEQ ID NO 124
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 4, 7
<223> OTHER INFORMATION: Xaa = Any Amino Acid

<400> SEQUENCE: 124

Gly Pro Ser Xaa Leu Trp Xaa
1               5

<210> SEQ ID NO 125
<211> LENGTH: 7
<212> TYPE: PRT
<213> ORGANISM: Artificial Sequence
<220> FEATURE:
<223> OTHER INFORMATION: binding peptide

<400> SEQUENCE: 125

Gly Val Pro Phe Ala Thr Pro
1               5

<210> SEQ ID NO 126
<211> LENGTH: 7
<212> TYPE: PRT
<213> ORGANISM: Artificial Sequence
<220> FEATURE:
<223> OTHER INFORMATION: binding peptide

<400> SEQUENCE: 126

His Asn Leu Arg Phe Ala His
1               5

<210> SEQ ID NO 127
<211> LENGTH: 7
<212> TYPE: PRT
<213> ORGANISM: Artificial Sequence
<220> FEATURE:
<223> OTHER INFORMATION: binding peptide

<400> SEQUENCE: 127

His Arg His Pro Pro Gly Leu
1               5

<210> SEQ ID NO 128
<211> LENGTH: 7
<212> TYPE: PRT
<213> ORGANISM: Artificial Sequence
<220> FEATURE:
<223> OTHER INFORMATION: binding peptide

<400> SEQUENCE: 128

His Thr Asp Gln Thr Ser Asp
1               5

<210> SEQ ID NO 129
<211> LENGTH: 12
```

```
<212> TYPE: PRT
<213> ORGANISM: Artificial Sequence
<220> FEATURE:
<223> OTHER INFORMATION: binding peptide
<221> NAME/KEY: VARIANT
<222> LOCATION: 2, 8
<223> OTHER INFORMATION: Xaa = Any Amino Acid

<400> SEQUENCE: 129

His Xaa Gly Pro Arg Leu Glu Xaa Ala Ser Asp Phe
 1               5                   10

<210> SEQ ID NO 130
<211> LENGTH: 11
<212> TYPE: PRT
<213> ORGANISM: Artificial Sequence
<220> FEATURE:
<223> OTHER INFORMATION: binding peptide

<400> SEQUENCE: 130

Ile Pro Leu Ile Lys Gly Met His Pro Pro Asp
 1               5                   10

<210> SEQ ID NO 131
<211> LENGTH: 7
<212> TYPE: PRT
<213> ORGANISM: Artificial Sequence
<220> FEATURE:
<223> OTHER INFORMATION: binding peptide

<400> SEQUENCE: 131

Ile Pro Thr Thr Arg Gln Thr
 1               5

<210> SEQ ID NO 132
<211> LENGTH: 7
<212> TYPE: PRT
<213> ORGANISM: Artificial Sequence
<220> FEATURE:
<223> OTHER INFORMATION: binding peptide

<400> SEQUENCE: 132

Lys Ala Ser His Leu Val Pro
 1               5

<210> SEQ ID NO 133
<211> LENGTH: 7
<212> TYPE: PRT
<213> ORGANISM: Artificial Sequence
<220> FEATURE:
<223> OTHER INFORMATION: binding peptide

<400> SEQUENCE: 133

Lys Asp Ala Lys Lys Ile Thr
 1               5

<210> SEQ ID NO 134
<211> LENGTH: 12
<212> TYPE: PRT
<213> ORGANISM: Artificial Sequence
<220> FEATURE:
<223> OTHER INFORMATION: binding peptide

<400> SEQUENCE: 134

Lys Asp Pro Ser Trp Pro Ser Gln Ala Gln Thr Pro
 1               5                   10

<210> SEQ ID NO 135
```

```
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 3, 7
<223> OTHER INFORMATION: Xaa = Any Amino Acid

<400> SEQUENCE: 135

Lys Pro Xaa Leu Pro Thr Xaa
1               5

<210> SEQ ID NO 136
<211> LENGTH: 7
<212> TYPE: PRT
<213> ORGANISM: Artificial Sequence
<220> FEATURE:
<223> OTHER INFORMATION: binding peptide

<400> SEQUENCE: 136

Leu Lys Glu Phe Gln Gln Ile
1               5

<210> SEQ ID NO 137
<211> LENGTH: 7
<212> TYPE: PRT
<213> ORGANISM: Artificial Sequence
<220> FEATURE:
<223> OTHER INFORMATION: binding peptide

<400> SEQUENCE: 137

Leu Leu Leu Ser Pro Pro Pro
1               5

<210> SEQ ID NO 138
<211> LENGTH: 7
<212> TYPE: PRT
<213> ORGANISM: Artificial Sequence
<220> FEATURE:
<223> OTHER INFORMATION: binding peptide

<400> SEQUENCE: 138

Leu Pro Lys His Thr Leu Thr
1               5

<210> SEQ ID NO 139
<211> LENGTH: 7
<212> TYPE: PRT
<213> ORGANISM: Artificial Sequence
<220> FEATURE:
<223> OTHER INFORMATION: binding peptide

<400> SEQUENCE: 139

Leu Pro Thr Ser Thr Leu Thr
1               5

<210> SEQ ID NO 140
<211> LENGTH: 7
<212> TYPE: PRT
<213> ORGANISM: Artificial Sequence
<220> FEATURE:
<223> OTHER INFORMATION: binding peptide

<400> SEQUENCE: 140

Leu Gln Asp Cys Leu Arg Asn
1               5
```

```
<210> SEQ ID NO 141
<211> LENGTH: 7
<212> TYPE: PRT
<213> ORGANISM: Artificial Sequence
<220> FEATURE:
<223> OTHER INFORMATION: binding peptide

<400> SEQUENCE: 141

Leu Ser Thr Pro Gly Met Gln
 1               5

<210> SEQ ID NO 142
<211> LENGTH: 7
<212> TYPE: PRT
<213> ORGANISM: Artificial Sequence
<220> FEATURE:
<223> OTHER INFORMATION: binding peptide

<400> SEQUENCE: 142

Leu Thr Pro Asp Ala Ile Phe
 1               5

<210> SEQ ID NO 143
<211> LENGTH: 7
<212> TYPE: PRT
<213> ORGANISM: Artificial Sequence
<220> FEATURE:
<223> OTHER INFORMATION: binding peptide

<400> SEQUENCE: 143

Met Val Gln Gly Thr Ser Glu
 1               5

<210> SEQ ID NO 144
<211> LENGTH: 7
<212> TYPE: PRT
<213> ORGANISM: Artificial Sequence
<220> FEATURE:
<223> OTHER INFORMATION: binding peptide

<400> SEQUENCE: 144

Asn Leu Lys Val Gln Gln Arg
 1               5

<210> SEQ ID NO 145
<211> LENGTH: 7
<212> TYPE: PRT
<213> ORGANISM: Artificial Sequence
<220> FEATURE:
<223> OTHER INFORMATION: binding peptide

<400> SEQUENCE: 145

Asn Ser Ala Pro His Val Thr
 1               5

<210> SEQ ID NO 146
<211> LENGTH: 7
<212> TYPE: PRT
<213> ORGANISM: Artificial Sequence
<220> FEATURE:
<223> OTHER INFORMATION: binding peptide

<400> SEQUENCE: 146

Asn Thr Asn Pro Phe Gln Pro
 1               5

<210> SEQ ID NO 147
<211> LENGTH: 7
```

```
<212> TYPE: PRT
<213> ORGANISM: Artificial Sequence
<220> FEATURE:
<223> OTHER INFORMATION: binding peptide

<400> SEQUENCE: 147

Asn Val Thr Met Val Leu Leu
 1               5

<210> SEQ ID NO 148
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 2, 7
<223> OTHER INFORMATION: Xaa = Any Amino Acid

<400> SEQUENCE: 148

Asn Xaa Lys Thr Ser Gln Xaa
 1               5

<210> SEQ ID NO 149
<211> LENGTH: 7
<212> TYPE: PRT
<213> ORGANISM: Artificial Sequence
<220> FEATURE:
<223> OTHER INFORMATION: binding peptide

<400> SEQUENCE: 149

Pro Gly Lys His Gly Gln Ala
 1               5

<210> SEQ ID NO 150
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 6
<223> OTHER INFORMATION: Xaa = Any Amino Acid

<400> SEQUENCE: 150

Pro Ile Thr Pro Val Xaa Ala
 1               5

<210> SEQ ID NO 151
<211> LENGTH: 7
<212> TYPE: PRT
<213> ORGANISM: Artificial Sequence
<220> FEATURE:
<223> OTHER INFORMATION: binding peptide

<400> SEQUENCE: 151

Pro Pro Ile Ile Asp Leu Glu
 1               5

<210> SEQ ID NO 152
<211> LENGTH: 7
<212> TYPE: PRT
<213> ORGANISM: Artificial Sequence
<220> FEATURE:
<223> OTHER INFORMATION: binding peptide

<400> SEQUENCE: 152

Pro Pro Ser Pro Leu Thr Pro
 1               5
```

```
<210> SEQ ID NO 153
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 3, 6, 7
<223> OTHER INFORMATION: Xaa = Any Amino Acid

<400> SEQUENCE: 153

Pro Gln Xaa Gly Ile Xaa Xaa
 1               5

<210> SEQ ID NO 154
<211> LENGTH: 7
<212> TYPE: PRT
<213> ORGANISM: Artificial Sequence
<220> FEATURE:
<223> OTHER INFORMATION: binding peptide

<400> SEQUENCE: 154

Pro Thr Leu Ala Gly Ala Ser
 1               5

<210> SEQ ID NO 155
<211> LENGTH: 7
<212> TYPE: PRT
<213> ORGANISM: Artificial Sequence
<220> FEATURE:
<223> OTHER INFORMATION: binding peptide

<400> SEQUENCE: 155

Pro Thr Leu Phe Lys Glu His
 1               5

<210> SEQ ID NO 156
<211> LENGTH: 7
<212> TYPE: PRT
<213> ORGANISM: Artificial Sequence
<220> FEATURE:
<223> OTHER INFORMATION: binding peptide

<400> SEQUENCE: 156

Pro Tyr Leu Ser Asp Lys Ala
 1               5

<210> SEQ ID NO 157
<211> LENGTH: 7
<212> TYPE: PRT
<213> ORGANISM: Artificial Sequence
<220> FEATURE:
<223> OTHER INFORMATION: binding peptide

<400> SEQUENCE: 157

Gln Asp Thr Ala Pro Leu Thr
 1               5

<210> SEQ ID NO 158
<211> LENGTH: 7
<212> TYPE: PRT
<213> ORGANISM: Artificial Sequence
<220> FEATURE:
<223> OTHER INFORMATION: binding peptide

<400> SEQUENCE: 158

Gln Asn Gln Lys Ser Thr Thr
```

```
<210> SEQ ID NO 159
<211> LENGTH: 7
<212> TYPE: PRT
<213> ORGANISM: Artificial Sequence
<220> FEATURE:
<223> OTHER INFORMATION: binding peptide

<400> SEQUENCE: 159

Gln Pro Gly His Leu Asp Ile
1               5

<210> SEQ ID NO 160
<211> LENGTH: 7
<212> TYPE: PRT
<213> ORGANISM: Artificial Sequence
<220> FEATURE:
<223> OTHER INFORMATION: binding peptide

<400> SEQUENCE: 160

Gln Ser Asp Met His Trp Arg
1               5

<210> SEQ ID NO 161
<211> LENGTH: 7
<212> TYPE: PRT
<213> ORGANISM: Artificial Sequence
<220> FEATURE:
<223> OTHER INFORMATION: binding peptide

<400> SEQUENCE: 161

Gln Ser Glu Pro His Pro Lys
1               5

<210> SEQ ID NO 162
<211> LENGTH: 7
<212> TYPE: PRT
<213> ORGANISM: Artificial Sequence
<220> FEATURE:
<223> OTHER INFORMATION: binding peptide

<400> SEQUENCE: 162

Arg Ala Gly Glu Ser His Arg
1               5

<210> SEQ ID NO 163
<211> LENGTH: 7
<212> TYPE: PRT
<213> ORGANISM: Artificial Sequence
<220> FEATURE:
<223> OTHER INFORMATION: binding peptide

<400> SEQUENCE: 163

Arg Asp Ala Tyr Leu Thr Pro
1               5

<210> SEQ ID NO 164
<211> LENGTH: 7
<212> TYPE: PRT
<213> ORGANISM: Artificial Sequence
<220> FEATURE:
<223> OTHER INFORMATION: binding peptide

<400> SEQUENCE: 164

Arg Leu Ser Leu Pro Met Gln
1               5
```

<210> SEQ ID NO 165
<211> LENGTH: 7
<212> TYPE: PRT
<213> ORGANISM: Artificial Sequence
<220> FEATURE:
<223> OTHER INFORMATION: binding peptide

<400> SEQUENCE: 165

Arg Met Ala Thr Pro Asn Ala
1               5

<210> SEQ ID NO 166
<211> LENGTH: 7
<212> TYPE: PRT
<213> ORGANISM: Artificial Sequence
<220> FEATURE:
<223> OTHER INFORMATION: binding peptide

<400> SEQUENCE: 166

Ser Ala Ser Ala Thr Trp Thr
1               5

<210> SEQ ID NO 167
<211> LENGTH: 7
<212> TYPE: PRT
<213> ORGANISM: Artificial Sequence
<220> FEATURE:
<223> OTHER INFORMATION: binding peptide

<400> SEQUENCE: 167

Ser Gly Pro Ala Asp Ala Asp
1               5

<210> SEQ ID NO 168
<211> LENGTH: 7
<212> TYPE: PRT
<213> ORGANISM: Artificial Sequence
<220> FEATURE:
<223> OTHER INFORMATION: binding peptide

<400> SEQUENCE: 168

Ser Ile Ile Pro Pro Arg Gln
1               5

<210> SEQ ID NO 169
<211> LENGTH: 7
<212> TYPE: PRT
<213> ORGANISM: Artificial Sequence
<220> FEATURE:
<223> OTHER INFORMATION: binding peptide

<400> SEQUENCE: 169

Ser Lys Asn Thr Ala Phe Gly
1               5

<210> SEQ ID NO 170
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 5
<223> OTHER INFORMATION: Xaa = Any Amino Acid

<400> SEQUENCE: 170

Ser Leu Ser Thr Xaa Ala Asn
1               5

```
<210> SEQ ID NO 171
<211> LENGTH: 7
<212> TYPE: PRT
<213> ORGANISM: Artificial Sequence
<220> FEATURE:
<223> OTHER INFORMATION: binding peptide

<400> SEQUENCE: 171

Ser Met Trp Gly Asn Leu His
 1               5

<210> SEQ ID NO 172
<211> LENGTH: 7
<212> TYPE: PRT
<213> ORGANISM: Artificial Sequence
<220> FEATURE:
<223> OTHER INFORMATION: binding peptide

<400> SEQUENCE: 172

Ser Asn His Leu Ile Gln Tyr
 1               5

<210> SEQ ID NO 173
<211> LENGTH: 7
<212> TYPE: PRT
<213> ORGANISM: Artificial Sequence
<220> FEATURE:
<223> OTHER INFORMATION: binding peptide

<400> SEQUENCE: 173

Ser Arg Ala Trp Ser Trp Pro
 1               5

<210> SEQ ID NO 174
<211> LENGTH: 7
<212> TYPE: PRT
<213> ORGANISM: Artificial Sequence
<220> FEATURE:
<223> OTHER INFORMATION: binding peptide

<400> SEQUENCE: 174

Ser Ser Leu Leu Pro Arg Ser
 1               5

<210> SEQ ID NO 175
<211> LENGTH: 7
<212> TYPE: PRT
<213> ORGANISM: Artificial Sequence
<220> FEATURE:
<223> OTHER INFORMATION: binding peptide

<400> SEQUENCE: 175

Ser Val Ser Leu Val Ser Leu
 1               5

<210> SEQ ID NO 176
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 2
<223> OTHER INFORMATION: Xaa = Any Amino Acid

<400> SEQUENCE: 176

Ser Xaa Thr Leu Ser Pro Tyr
```

```
<210> SEQ ID NO 177
<211> LENGTH: 7
<212> TYPE: PRT
<213> ORGANISM: Artificial Sequence
<220> FEATURE:
<223> OTHER INFORMATION: binding peptide

<400> SEQUENCE: 177

Thr Ala Pro Leu Ile Ser Ile
1               5

<210> SEQ ID NO 178
<211> LENGTH: 7
<212> TYPE: PRT
<213> ORGANISM: Artificial Sequence
<220> FEATURE:
<223> OTHER INFORMATION: binding peptide

<400> SEQUENCE: 178

Thr Ile Gln Ser Arg Tyr Thr
1               5

<210> SEQ ID NO 179
<211> LENGTH: 7
<212> TYPE: PRT
<213> ORGANISM: Artificial Sequence
<220> FEATURE:
<223> OTHER INFORMATION: binding peptide

<400> SEQUENCE: 179

Thr Lys Ser Ser Met Pro Thr
1               5

<210> SEQ ID NO 180
<211> LENGTH: 7
<212> TYPE: PRT
<213> ORGANISM: Artificial Sequence
<220> FEATURE:
<223> OTHER INFORMATION: binding peptide

<400> SEQUENCE: 180

Thr Lys Thr Thr Trp Gln Thr
1               5

<210> SEQ ID NO 181
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 7
<223> OTHER INFORMATION: Xaa = Any Amino Acid

<400> SEQUENCE: 181

Thr Leu Phe Tyr Thr Lys Xaa
1               5

<210> SEQ ID NO 182
<211> LENGTH: 7
<212> TYPE: PRT
<213> ORGANISM: Artificial Sequence
<220> FEATURE:
<223> OTHER INFORMATION: binding peptide

<400> SEQUENCE: 182
```

```
Thr Gln Arg Leu Thr Thr His
1               5

<210> SEQ ID NO 183
<211> LENGTH: 7
<212> TYPE: PRT
<213> ORGANISM: Artificial Sequence
<220> FEATURE:
<223> OTHER INFORMATION: binding peptide

<400> SEQUENCE: 183

Thr Arg Glu Ser Gly Glu Gln
1               5

<210> SEQ ID NO 184
<211> LENGTH: 7
<212> TYPE: PRT
<213> ORGANISM: Artificial Sequence
<220> FEATURE:
<223> OTHER INFORMATION: binding peptide

<400> SEQUENCE: 184

Thr Ser Leu Val Pro Asp Lys
1               5

<210> SEQ ID NO 185
<211> LENGTH: 7
<212> TYPE: PRT
<213> ORGANISM: Artificial Sequence
<220> FEATURE:
<223> OTHER INFORMATION: binding peptide

<400> SEQUENCE: 185

Thr Thr Met Ala Tyr Val Ala
1               5

<210> SEQ ID NO 186
<211> LENGTH: 7
<212> TYPE: PRT
<213> ORGANISM: Artificial Sequence
<220> FEATURE:
<223> OTHER INFORMATION: binding peptide

<400> SEQUENCE: 186

Thr Val Pro Met Arg Ser Leu
1               5

<210> SEQ ID NO 187
<211> LENGTH: 12
<212> TYPE: PRT
<213> ORGANISM: Artificial Sequence
<220> FEATURE:
<223> OTHER INFORMATION: binding peptide
<221> NAME/KEY: VARIANT
<222> LOCATION: 11
<223> OTHER INFORMATION: Xaa = Any Amino Acid

<400> SEQUENCE: 187

Val Asp Arg Asn Gln Ser Leu Arg Ser Phe Xaa Thr
1               5                   10

<210> SEQ ID NO 188
<211> LENGTH: 7
<212> TYPE: PRT
<213> ORGANISM: Artificial Sequence
<220> FEATURE:
<223> OTHER INFORMATION: binding peptide

<400> SEQUENCE: 188
```

Val Gly Gln Gly Asn Thr Ser
1               5

<210> SEQ ID NO 189
<211> LENGTH: 7
<212> TYPE: PRT
<213> ORGANISM: Artificial Sequence
<220> FEATURE:
<223> OTHER INFORMATION: binding peptide

<400> SEQUENCE: 189

Val Leu Pro Met Tyr Ser His
1               5

<210> SEQ ID NO 190
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 5
<223> OTHER INFORMATION: Xaa = Any Amino Acid

<400> SEQUENCE: 190

Trp Leu Arg Pro Xaa Leu His
1               5

<210> SEQ ID NO 191
<211> LENGTH: 7
<212> TYPE: PRT
<213> ORGANISM: Artificial Sequence
<220> FEATURE:
<223> OTHER INFORMATION: binding peptide

<400> SEQUENCE: 191

Trp Gln Leu Ala Arg Pro Lys
1               5

<210> SEQ ID NO 192
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 4
<223> OTHER INFORMATION: Xaa = Any Amino Acid

<400> SEQUENCE: 192

Trp Gln Thr Xaa Leu Thr Asp
1               5

<210> SEQ ID NO 193
<211> LENGTH: 12
<212> TYPE: PRT
<213> ORGANISM: Artificial Sequence
<220> FEATURE:
<223> OTHER INFORMATION: binding peptide

<400> SEQUENCE: 193

Trp Ser Asn Lys Pro Leu Ser Pro Asn Asp Leu Arg
1               5                   10

<210> SEQ ID NO 194
<211> LENGTH: 7
<212> TYPE: PRT
<213> ORGANISM: Artificial Sequence

```
<220> FEATURE:
<223> OTHER INFORMATION: binding peptide
<221> NAME/KEY: VARIANT
<222> LOCATION: 1
<223> OTHER INFORMATION: Xaa = Any Amino Acid

<400> SEQUENCE: 194

Xaa Ala Leu Pro Trp Lys Ser
 1               5

<210> SEQ ID NO 195
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 1, 4, 6, 7
<223> OTHER INFORMATION: Xaa = Any Amino Acid

<400> SEQUENCE: 195

Xaa Asp Ser Xaa Ser Xaa Xaa
 1               5

<210> SEQ ID NO 196
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 1
<223> OTHER INFORMATION: Xaa = Any Amino Acid

<400> SEQUENCE: 196

Xaa Pro Thr Val Asp Asn His
 1               5

<210> SEQ ID NO 197
<211> LENGTH: 7
<212> TYPE: PRT
<213> ORGANISM: Artificial Sequence
<220> FEATURE:
<223> OTHER INFORMATION: binding peptide
<221> NAME/KEY: VARIANT
<222> LOCATION: 1, 3, 4, 7
<223> OTHER INFORMATION: Xaa = Any Amino Acid

<400> SEQUENCE: 197

Xaa Pro Xaa Xaa Val Phe Xaa
 1               5

<210> SEQ ID NO 198
<211> LENGTH: 7
<212> TYPE: PRT
<213> ORGANISM: Artificial Sequence
<220> FEATURE:
<223> OTHER INFORMATION: binding peptide

<400> SEQUENCE: 198

Tyr Ala Asp Ser Val Gln Met
 1               5

<210> SEQ ID NO 199
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 199

Tyr Pro Ala Pro Lys Pro Tyr
1               5

<210> SEQ ID NO 200
<211> LENGTH: 12
<212> TYPE: PRT
<213> ORGANISM: Artificial Sequence
<220> FEATURE:
<223> OTHER INFORMATION: binding peptide
<221> NAME/KEY: VARIANT
<222> LOCATION: 4
<223> OTHER INFORMATION: Xaa = Any Amino Acid

<400> SEQUENCE: 200

Tyr Ser Ile Xaa Val Met Gly Tyr Tyr Thr Pro Tyr
1               5                   10

<210> SEQ ID NO 201
<211> LENGTH: 7
<212> TYPE: PRT
<213> ORGANISM: Artificial Sequence
<220> FEATURE:
<223> OTHER INFORMATION: binding peptide

<400> SEQUENCE: 201

Tyr Thr Lys Thr Ser Gln Tyr
1               5

<210> SEQ ID NO 202
<211> LENGTH: 7
<212> TYPE: PRT
<213> ORGANISM: Artificial Sequence
<220> FEATURE:
<223> OTHER INFORMATION: binding peptide

<400> SEQUENCE: 202

Ala Asp Lys Thr Lys Asn Tyr
1               5

<210> SEQ ID NO 203
<211> LENGTH: 7
<212> TYPE: PRT
<213> ORGANISM: Artificial Sequence
<220> FEATURE:
<223> OTHER INFORMATION: binding peptide

<400> SEQUENCE: 203

Gln Tyr His Gly Pro Leu Pro
1               5

<210> SEQ ID NO 204
<211> LENGTH: 7
<212> TYPE: PRT
<213> ORGANISM: Artificial Sequence
<220> FEATURE:
<223> OTHER INFORMATION: binding peptide

<400> SEQUENCE: 204

Thr Pro Pro Met Gly Arg His
1               5

<210> SEQ ID NO 205
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 205

His Pro Thr Ala Gln Thr Leu
1               5

<210> SEQ ID NO 206
<211> LENGTH: 7
<212> TYPE: PRT
<213> ORGANISM: Artificial Sequence
<220> FEATURE:
<223> OTHER INFORMATION: binding peptide

<400> SEQUENCE: 206

Ser Asp Glu Ser Met Asn Met
1               5

<210> SEQ ID NO 207
<211> LENGTH: 7
<212> TYPE: PRT
<213> ORGANISM: Artificial Sequence
<220> FEATURE:
<223> OTHER INFORMATION: binding peptide

<400> SEQUENCE: 207

Ser His Phe Ser Gly Asn Arg
1               5

<210> SEQ ID NO 208
<211> LENGTH: 7
<212> TYPE: PRT
<213> ORGANISM: Artificial Sequence
<220> FEATURE:
<223> OTHER INFORMATION: binding peptide

<400> SEQUENCE: 208

Asp His Asn Gln Thr Asn Arg
1               5

<210> SEQ ID NO 209
<211> LENGTH: 7
<212> TYPE: PRT
<213> ORGANISM: Artificial Sequence
<220> FEATURE:
<223> OTHER INFORMATION: binding peptide

<400> SEQUENCE: 209

Leu His Thr His Ser Asn Thr
1               5

<210> SEQ ID NO 210
<211> LENGTH: 7
<212> TYPE: PRT
<213> ORGANISM: Artificial Sequence
<220> FEATURE:
<223> OTHER INFORMATION: binding peptide

<400> SEQUENCE: 210

Asn Gly Asn Phe Asp Ser Ala
1               5

<210> SEQ ID NO 211
<211> LENGTH: 7
<212> TYPE: PRT
<213> ORGANISM: Artificial Sequence
<220> FEATURE:
<223> OTHER INFORMATION: binding peptide

<400> SEQUENCE: 211
```

Arg Pro Leu Met Ser Thr Gln
1               5

<210> SEQ ID NO 212
<211> LENGTH: 7
<212> TYPE: PRT
<213> ORGANISM: Artificial Sequence
<220> FEATURE:
<223> OTHER INFORMATION: binding peptide

<400> SEQUENCE: 212

Val Asn Asp Pro Thr Thr Ile
1               5

<210> SEQ ID NO 213
<211> LENGTH: 7
<212> TYPE: PRT
<213> ORGANISM: Artificial Sequence
<220> FEATURE:
<223> OTHER INFORMATION: binding peptide

<400> SEQUENCE: 213

Thr Gly Asn Ser Ser Gln Gln
1               5

<210> SEQ ID NO 214
<211> LENGTH: 7
<212> TYPE: PRT
<213> ORGANISM: Artificial Sequence
<220> FEATURE:
<223> OTHER INFORMATION: binding peptide

<400> SEQUENCE: 214

Lys Ser Thr Leu Tyr His Thr
1               5

<210> SEQ ID NO 215
<211> LENGTH: 7
<212> TYPE: PRT
<213> ORGANISM: Artificial Sequence
<220> FEATURE:
<223> OTHER INFORMATION: binding peptide

<400> SEQUENCE: 215

Lys Ala Ala His Asp Glu Gly
1               5

<210> SEQ ID NO 216
<211> LENGTH: 7
<212> TYPE: PRT
<213> ORGANISM: Artificial Sequence
<220> FEATURE:
<223> OTHER INFORMATION: binding peptide

<400> SEQUENCE: 216

Trp His Thr Gly Pro Ser Glu
1               5

<210> SEQ ID NO 217
<211> LENGTH: 7
<212> TYPE: PRT
<213> ORGANISM: Artificial Sequence
<220> FEATURE:
<223> OTHER INFORMATION: binding peptide

<400> SEQUENCE: 217

Ile Thr Gln Glu Arg Asn Gln

<210> SEQ ID NO 218
<211> LENGTH: 7
<212> TYPE: PRT
<213> ORGANISM: Artificial Sequence
<220> FEATURE:
<223> OTHER INFORMATION: binding peptide

<400> SEQUENCE: 218

Gly Asn Asp Gln Val Ser Pro
1               5

<210> SEQ ID NO 219
<211> LENGTH: 7
<212> TYPE: PRT
<213> ORGANISM: Artificial Sequence
<220> FEATURE:
<223> OTHER INFORMATION: binding peptide

<400> SEQUENCE: 219

Leu Thr Asp Ser Phe Leu Gly
1               5

<210> SEQ ID NO 220
<211> LENGTH: 7
<212> TYPE: PRT
<213> ORGANISM: Artificial Sequence
<220> FEATURE:
<223> OTHER INFORMATION: binding peptide

<400> SEQUENCE: 220

Pro Tyr Thr Trp His Leu Glu
1               5

<210> SEQ ID NO 221
<211> LENGTH: 7
<212> TYPE: PRT
<213> ORGANISM: Artificial Sequence
<220> FEATURE:
<223> OTHER INFORMATION: binding peptide

<400> SEQUENCE: 221

Ala Thr Asp Asn Thr Leu Gln
1               5

<210> SEQ ID NO 222
<211> LENGTH: 7
<212> TYPE: PRT
<213> ORGANISM: Artificial Sequence
<220> FEATURE:
<223> OTHER INFORMATION: binding peptide

<400> SEQUENCE: 222

Pro Val Ser Met Ile Ser Thr
1               5

<210> SEQ ID NO 223
<211> LENGTH: 7
<212> TYPE: PRT
<213> ORGANISM: Artificial Sequence
<220> FEATURE:
<223> OTHER INFORMATION: binding peptide

<400> SEQUENCE: 223

Leu Asn Lys Thr Ser Pro Asn
1               5

```
<210> SEQ ID NO 224
<211> LENGTH: 12
<212> TYPE: PRT
<213> ORGANISM: Artificial Sequence
<220> FEATURE:
<223> OTHER INFORMATION: binding peptide

<400> SEQUENCE: 224

Ser Ser Tyr Gln Ile Asn Thr Thr Pro Ala Leu Pro
1               5                   10

<210> SEQ ID NO 225
<211> LENGTH: 12
<212> TYPE: PRT
<213> ORGANISM: Artificial Sequence
<220> FEATURE:
<223> OTHER INFORMATION: binding peptide

<400> SEQUENCE: 225

Leu Pro Leu Gln Pro Leu Met Pro Pro Leu Asn Gln
1               5                   10

<210> SEQ ID NO 226
<211> LENGTH: 12
<212> TYPE: PRT
<213> ORGANISM: Artificial Sequence
<220> FEATURE:
<223> OTHER INFORMATION: binding peptide

<400> SEQUENCE: 226

Phe Tyr Phe Pro Gln Asn Leu Val Tyr Gln Ala Gly
1               5                   10

<210> SEQ ID NO 227
<211> LENGTH: 12
<212> TYPE: PRT
<213> ORGANISM: Artificial Sequence
<220> FEATURE:
<223> OTHER INFORMATION: binding peptide

<400> SEQUENCE: 227

Asn Ser Ser Pro Phe Ala Thr Met Pro Asn Ala Leu
1               5                   10

<210> SEQ ID NO 228
<211> LENGTH: 12
<212> TYPE: PRT
<213> ORGANISM: Artificial Sequence
<220> FEATURE:
<223> OTHER INFORMATION: binding peptide

<400> SEQUENCE: 228

Thr Cys Asn Ala Met Ser Ser Leu Cys Asp Pro Pro
1               5                   10

<210> SEQ ID NO 229
<211> LENGTH: 12
<212> TYPE: PRT
<213> ORGANISM: Artificial Sequence
<220> FEATURE:
<223> OTHER INFORMATION: binding peptide

<400> SEQUENCE: 229

Ser Pro Leu Pro Pro Leu Val Gly Ser Leu Leu Lys
1               5                   10

<210> SEQ ID NO 230
```

```
<211> LENGTH: 12
<212> TYPE: PRT
<213> ORGANISM: Artificial Sequence
<220> FEATURE:
<223> OTHER INFORMATION: binding peptide

<400> SEQUENCE: 230

Phe Pro Thr Lys His Thr Leu Ser Thr Thr Ile Tyr
 1               5                  10

<210> SEQ ID NO 231
<211> LENGTH: 12
<212> TYPE: PRT
<213> ORGANISM: Artificial Sequence
<220> FEATURE:
<223> OTHER INFORMATION: binding peptide

<400> SEQUENCE: 231

His Gly Pro Arg Pro Pro Gly Met Thr Leu Pro Ile
 1               5                  10

<210> SEQ ID NO 232
<211> LENGTH: 11
<212> TYPE: PRT
<213> ORGANISM: Artificial Sequence
<220> FEATURE:
<223> OTHER INFORMATION: binding peptide

<400> SEQUENCE: 232

Ser Pro Leu Leu Thr Tyr Lys Gln Gln Ala Leu
 1               5                  10

<210> SEQ ID NO 233
<211> LENGTH: 12
<212> TYPE: PRT
<213> ORGANISM: Artificial Sequence
<220> FEATURE:
<223> OTHER INFORMATION: binding peptide

<400> SEQUENCE: 233

Lys Leu Pro Tyr Pro Phe Pro Pro Glu Ala Met Val
 1               5                  10

<210> SEQ ID NO 234
<211> LENGTH: 12
<212> TYPE: PRT
<213> ORGANISM: Artificial Sequence
<220> FEATURE:
<223> OTHER INFORMATION: binding peptide

<400> SEQUENCE: 234

His Pro Phe Leu Pro Pro Ser Lys Thr Ala Pro Pro
 1               5                  10

<210> SEQ ID NO 235
<211> LENGTH: 12
<212> TYPE: PRT
<213> ORGANISM: Artificial Sequence
<220> FEATURE:
<223> OTHER INFORMATION: binding peptide
<221> NAME/KEY: VARIANT
<222> LOCATION: 3
<223> OTHER INFORMATION: Xaa = Any Amino Acid

<400> SEQUENCE: 235

Trp Thr Xaa Cys Val Glu Cys Thr Phe Ala Thr Pro
 1               5                  10
```

```
<210> SEQ ID NO 236
<211> LENGTH: 12
<212> TYPE: PRT
<213> ORGANISM: Artificial Sequence
<220> FEATURE:
<223> OTHER INFORMATION: binding peptide

<400> SEQUENCE: 236

Gly Ala Lys His Tyr Ala Arg Val Ala Ala Glu Phe
1               5                   10

<210> SEQ ID NO 237
<211> LENGTH: 12
<212> TYPE: PRT
<213> ORGANISM: Artificial Sequence
<220> FEATURE:
<223> OTHER INFORMATION: binding peptide

<400> SEQUENCE: 237

Gly Ile Met Gln Ser Thr Pro Pro Ala Asn Gln Gln
1               5                   10

<210> SEQ ID NO 238
<211> LENGTH: 12
<212> TYPE: PRT
<213> ORGANISM: Artificial Sequence
<220> FEATURE:
<223> OTHER INFORMATION: binding peptide

<400> SEQUENCE: 238

Tyr Gly Thr Gln Gln Gln Asp Arg Leu His Lys Pro
1               5                   10

<210> SEQ ID NO 239
<211> LENGTH: 12
<212> TYPE: PRT
<213> ORGANISM: Artificial Sequence
<220> FEATURE:
<223> OTHER INFORMATION: binding peptide

<400> SEQUENCE: 239

Val Asp Glu Phe Leu His Ala Met Pro Leu Asn Ala
1               5                   10

<210> SEQ ID NO 240
<211> LENGTH: 12
<212> TYPE: PRT
<213> ORGANISM: Artificial Sequence
<220> FEATURE:
<223> OTHER INFORMATION: binding peptide

<400> SEQUENCE: 240

His Met Pro His Pro Ala Thr Val His Leu Leu Trp
1               5                   10

<210> SEQ ID NO 241
<211> LENGTH: 12
<212> TYPE: PRT
<213> ORGANISM: Artificial Sequence
<220> FEATURE:
<223> OTHER INFORMATION: binding peptide

<400> SEQUENCE: 241

Arg Ala Ala Thr Ala Glu Leu Pro Gly Gly Arg Val
1               5                   10

<210> SEQ ID NO 242
<211> LENGTH: 12
```

```
<212> TYPE: PRT
<213> ORGANISM: Artificial Sequence
<220> FEATURE:
<223> OTHER INFORMATION: binding peptide

<400> SEQUENCE: 242

Leu Ile Glu Pro Tyr Thr Arg Ser Ala Asn Ser Phe
1               5                   10

<210> SEQ ID NO 243
<211> LENGTH: 12
<212> TYPE: PRT
<213> ORGANISM: Artificial Sequence
<220> FEATURE:
<223> OTHER INFORMATION: binding peptide

<400> SEQUENCE: 243

Asp Val Asp Gln Leu Arg Ser Ala Val Trp Ser Arg
1               5                   10

<210> SEQ ID NO 244
<211> LENGTH: 7
<212> TYPE: PRT
<213> ORGANISM: Artificial Sequence
<220> FEATURE:
<223> OTHER INFORMATION: binding peptide

<400> SEQUENCE: 244

Leu Ser Val Thr Thr Asn Thr
1               5

<210> SEQ ID NO 245
<211> LENGTH: 7
<212> TYPE: PRT
<213> ORGANISM: Artificial Sequence
<220> FEATURE:
<223> OTHER INFORMATION: binding peptide

<400> SEQUENCE: 245

Asp Ser Leu Phe Lys Trp Thr
1               5

<210> SEQ ID NO 246
<211> LENGTH: 7
<212> TYPE: PRT
<213> ORGANISM: Artificial Sequence
<220> FEATURE:
<223> OTHER INFORMATION: binding peptide

<400> SEQUENCE: 246

Phe Glu Thr Lys Ala Asn Asp
1               5

<210> SEQ ID NO 247
<211> LENGTH: 7
<212> TYPE: PRT
<213> ORGANISM: Artificial Sequence
<220> FEATURE:
<223> OTHER INFORMATION: binding peptide

<400> SEQUENCE: 247

Asn Val Asn Asn His Ile His
1               5

<210> SEQ ID NO 248
<211> LENGTH: 7
<212> TYPE: PRT
<213> ORGANISM: Artificial Sequence
```

```
<220> FEATURE:
<223> OTHER INFORMATION: binding peptide

<400> SEQUENCE: 248

Gln Pro Ala Lys Gly Val Leu
1               5

<210> SEQ ID NO 249
<211> LENGTH: 7
<212> TYPE: PRT
<213> ORGANISM: Artificial Sequence
<220> FEATURE:
<223> OTHER INFORMATION: binding peptide

<400> SEQUENCE: 249

Asp Tyr Ala His Gly Asn Thr
1               5

<210> SEQ ID NO 250
<211> LENGTH: 7
<212> TYPE: PRT
<213> ORGANISM: Artificial Sequence
<220> FEATURE:
<223> OTHER INFORMATION: binding peptide

<400> SEQUENCE: 250

Ser Arg Ser Glu Leu Pro Leu
1               5

<210> SEQ ID NO 251
<211> LENGTH: 7
<212> TYPE: PRT
<213> ORGANISM: Artificial Sequence
<220> FEATURE:
<223> OTHER INFORMATION: binding peptide

<400> SEQUENCE: 251

Ala Asp Arg Leu Arg Pro Thr
1               5

<210> SEQ ID NO 252
<211> LENGTH: 7
<212> TYPE: PRT
<213> ORGANISM: Artificial Sequence
<220> FEATURE:
<223> OTHER INFORMATION: binding peptide

<400> SEQUENCE: 252

His Ser Pro Gln Met Gln Ser
1               5

<210> SEQ ID NO 253
<211> LENGTH: 7
<212> TYPE: PRT
<213> ORGANISM: Artificial Sequence
<220> FEATURE:
<223> OTHER INFORMATION: binding peptide

<400> SEQUENCE: 253

Asn Leu Ala Arg Asp Gly Thr
1               5

<210> SEQ ID NO 254
<211> LENGTH: 7
<212> TYPE: PRT
<213> ORGANISM: Artificial Sequence
<220> FEATURE:
<223> OTHER INFORMATION: binding peptide
```

<400> SEQUENCE: 254

Thr Gly Asn Lys Ser Ser Met
1               5

<210> SEQ ID NO 255
<211> LENGTH: 7
<212> TYPE: PRT
<213> ORGANISM: Artificial Sequence
<220> FEATURE:
<223> OTHER INFORMATION: binding peptide

<400> SEQUENCE: 255

Thr Lys Asp Ala Trp Pro Ser
1               5

<210> SEQ ID NO 256
<211> LENGTH: 7
<212> TYPE: PRT
<213> ORGANISM: Artificial Sequence
<220> FEATURE:
<223> OTHER INFORMATION: binding peptide

<400> SEQUENCE: 256

Ser Pro Ala Leu Val Asn Ser
1               5

<210> SEQ ID NO 257
<211> LENGTH: 7
<212> TYPE: PRT
<213> ORGANISM: Artificial Sequence
<220> FEATURE:
<223> OTHER INFORMATION: binding peptide

<400> SEQUENCE: 257

Val Asn Ser Asp Asn Ala Tyr
1               5

<210> SEQ ID NO 258
<211> LENGTH: 7
<212> TYPE: PRT
<213> ORGANISM: Artificial Sequence
<220> FEATURE:
<223> OTHER INFORMATION: binding peptide

<400> SEQUENCE: 258

Thr Ala Glu Val Thr Arg Gly
1               5

<210> SEQ ID NO 259
<211> LENGTH: 7
<212> TYPE: PRT
<213> ORGANISM: Artificial Sequence
<220> FEATURE:
<223> OTHER INFORMATION: binding peptide

<400> SEQUENCE: 259

Thr Asn Lys Ile Pro Pro Leu
1               5

<210> SEQ ID NO 260
<211> LENGTH: 7
<212> TYPE: PRT
<213> ORGANISM: Artificial Sequence
<220> FEATURE:
<223> OTHER INFORMATION: binding peptide

<400> SEQUENCE: 260

Thr Asn Pro Asn His Ile Met
1               5

<210> SEQ ID NO 261
<211> LENGTH: 7
<212> TYPE: PRT
<213> ORGANISM: Artificial Sequence
<220> FEATURE:
<223> OTHER INFORMATION: binding peptide

<400> SEQUENCE: 261

Ser Ser Ala Thr Ser Ile Thr
1               5

<210> SEQ ID NO 262
<211> LENGTH: 7
<212> TYPE: PRT
<213> ORGANISM: Artificial Sequence
<220> FEATURE:
<223> OTHER INFORMATION: binding peptide

<400> SEQUENCE: 262

Gln Pro Leu Lys Thr Lys Gln
1               5

<210> SEQ ID NO 263
<211> LENGTH: 7
<212> TYPE: PRT
<213> ORGANISM: Artificial Sequence
<220> FEATURE:
<223> OTHER INFORMATION: binding peptide

<400> SEQUENCE: 263

Ile Glu Ser Arg Ser Met Gln
1               5

<210> SEQ ID NO 264
<211> LENGTH: 7
<212> TYPE: PRT
<213> ORGANISM: Artificial Sequence
<220> FEATURE:
<223> OTHER INFORMATION: binding peptide

<400> SEQUENCE: 264

Ser Phe Lys Ser Met Thr Phe
1               5

<210> SEQ ID NO 265
<211> LENGTH: 7
<212> TYPE: PRT
<213> ORGANISM: Artificial Sequence
<220> FEATURE:
<223> OTHER INFORMATION: binding peptide

<400> SEQUENCE: 265

His Ser Leu Met Met Pro Asn
1               5

<210> SEQ ID NO 266
<211> LENGTH: 7
<212> TYPE: PRT
<213> ORGANISM: Artificial Sequence
<220> FEATURE:
<223> OTHER INFORMATION: binding peptide

<400> SEQUENCE: 266

Thr Lys Ser Pro Thr Ala Ile

<210> SEQ ID NO 267
<211> LENGTH: 7
<212> TYPE: PRT
<213> ORGANISM: Artificial Sequence
<220> FEATURE:
<223> OTHER INFORMATION: binding peptide

<400> SEQUENCE: 267

Leu Ala Ser Glu Asn Met Asn
1               5

<210> SEQ ID NO 268
<211> LENGTH: 7
<212> TYPE: PRT
<213> ORGANISM: Artificial Sequence
<220> FEATURE:
<223> OTHER INFORMATION: binding peptide

<400> SEQUENCE: 268

Pro Pro His Ser His Gln Leu
1               5

<210> SEQ ID NO 269
<211> LENGTH: 7
<212> TYPE: PRT
<213> ORGANISM: Artificial Sequence
<220> FEATURE:
<223> OTHER INFORMATION: binding peptide

<400> SEQUENCE: 269

Gln Val Asn Tyr Thr Ser Val
1               5

<210> SEQ ID NO 270
<211> LENGTH: 7
<212> TYPE: PRT
<213> ORGANISM: Artificial Sequence
<220> FEATURE:
<223> OTHER INFORMATION: binding peptide

<400> SEQUENCE: 270

Lys Ser Pro Glu Tyr Pro Phe
1               5

<210> SEQ ID NO 271
<211> LENGTH: 7
<212> TYPE: PRT
<213> ORGANISM: Artificial Sequence
<220> FEATURE:
<223> OTHER INFORMATION: binding peptide

<400> SEQUENCE: 271

Lys Ala Pro His Gln Lys Ala
1               5

<210> SEQ ID NO 272
<211> LENGTH: 7
<212> TYPE: PRT
<213> ORGANISM: Artificial Sequence
<220> FEATURE:
<223> OTHER INFORMATION: binding peptide

<400> SEQUENCE: 272

Thr Arg Ser Pro Ser Tyr Leu
1               5

```
<210> SEQ ID NO 273
<211> LENGTH: 7
<212> TYPE: PRT
<213> ORGANISM: Artificial Sequence
<220> FEATURE:
<223> OTHER INFORMATION: binding peptide

<400> SEQUENCE: 273

Pro Asn Pro Trp Asn Ala Phe
1               5

<210> SEQ ID NO 274
<211> LENGTH: 7
<212> TYPE: PRT
<213> ORGANISM: Artificial Sequence
<220> FEATURE:
<223> OTHER INFORMATION: binding peptide

<400> SEQUENCE: 274

Pro Ser Ser His Ser Tyr Arg
1               5

<210> SEQ ID NO 275
<211> LENGTH: 7
<212> TYPE: PRT
<213> ORGANISM: Artificial Sequence
<220> FEATURE:
<223> OTHER INFORMATION: binding peptide

<400> SEQUENCE: 275

Lys Val Asn Met Leu His Asp
1               5

<210> SEQ ID NO 276
<211> LENGTH: 7
<212> TYPE: PRT
<213> ORGANISM: Artificial Sequence
<220> FEATURE:
<223> OTHER INFORMATION: binding peptide

<400> SEQUENCE: 276

Thr Ala His Ala Met His Leu
1               5

<210> SEQ ID NO 277
<211> LENGTH: 7
<212> TYPE: PRT
<213> ORGANISM: Artificial Sequence
<220> FEATURE:
<223> OTHER INFORMATION: binding peptide

<400> SEQUENCE: 277

His Pro Gly Leu Ser Asn Lys
1               5

<210> SEQ ID NO 278
<211> LENGTH: 7
<212> TYPE: PRT
<213> ORGANISM: Artificial Sequence
<220> FEATURE:
<223> OTHER INFORMATION: binding peptide

<400> SEQUENCE: 278

Val Pro Ile Asn Ser Ser Val
1               5

<210> SEQ ID NO 279
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 279

Lys Ser Asn Asn Thr Gly Tyr
1               5

<210> SEQ ID NO 280
<211> LENGTH: 7
<212> TYPE: PRT
<213> ORGANISM: Artificial Sequence
<220> FEATURE:
<223> OTHER INFORMATION: binding peptide

<400> SEQUENCE: 280

Leu Trp Asn Ala Lys Leu Ala
1               5

<210> SEQ ID NO 281
<211> LENGTH: 7
<212> TYPE: PRT
<213> ORGANISM: Artificial Sequence
<220> FEATURE:
<223> OTHER INFORMATION: binding peptide

<400> SEQUENCE: 281

Gln Met Thr Gln Thr Gln Ser
1               5

<210> SEQ ID NO 282
<211> LENGTH: 7
<212> TYPE: PRT
<213> ORGANISM: Artificial Sequence
<220> FEATURE:
<223> OTHER INFORMATION: binding peptide

<400> SEQUENCE: 282

Thr Ser Gly Pro His Pro Leu
1               5

<210> SEQ ID NO 283
<211> LENGTH: 7
<212> TYPE: PRT
<213> ORGANISM: Artificial Sequence
<220> FEATURE:
<223> OTHER INFORMATION: binding peptide

<400> SEQUENCE: 283

Asn Glu Ala Leu Gly His Leu
1               5

<210> SEQ ID NO 284
<211> LENGTH: 7
<212> TYPE: PRT
<213> ORGANISM: Artificial Sequence
<220> FEATURE:
<223> OTHER INFORMATION: binding peptide

<400> SEQUENCE: 284

Ser Gly Leu Ser Lys Leu Asn
1               5

<210> SEQ ID NO 285
<211> LENGTH: 7
<212> TYPE: PRT
```

<213> ORGANISM: Artificial Sequence
<220> FEATURE:
<223> OTHER INFORMATION: binding peptide

<400> SEQUENCE: 285

Lys His Ala Asp Ser Thr Ser
1               5

<210> SEQ ID NO 286
<211> LENGTH: 7
<212> TYPE: PRT
<213> ORGANISM: Artificial Sequence
<220> FEATURE:
<223> OTHER INFORMATION: binding peptide

<400> SEQUENCE: 286

Ser Thr Ser Gln His Asn Val
1               5

<210> SEQ ID NO 287
<211> LENGTH: 7
<212> TYPE: PRT
<213> ORGANISM: Artificial Sequence
<220> FEATURE:
<223> OTHER INFORMATION: binding peptide

<400> SEQUENCE: 287

Thr Thr Gln Thr Asn Lys Asp
1               5

<210> SEQ ID NO 288
<211> LENGTH: 7
<212> TYPE: PRT
<213> ORGANISM: Artificial Sequence
<220> FEATURE:
<223> OTHER INFORMATION: binding peptide

<400> SEQUENCE: 288

Asn Thr Ala Ala Thr Gly Thr
1               5

<210> SEQ ID NO 289
<211> LENGTH: 7
<212> TYPE: PRT
<213> ORGANISM: Artificial Sequence
<220> FEATURE:
<223> OTHER INFORMATION: binding peptide

<400> SEQUENCE: 289

Pro Ala Thr Asn Pro Asn His
1               5

<210> SEQ ID NO 290
<211> LENGTH: 7
<212> TYPE: PRT
<213> ORGANISM: Artificial Sequence
<220> FEATURE:
<223> OTHER INFORMATION: binding peptide

<400> SEQUENCE: 290

Leu Ala Glu Thr His Ser Ser
1               5

<210> SEQ ID NO 291
<211> LENGTH: 7
<212> TYPE: PRT
<213> ORGANISM: Artificial Sequence
<220> FEATURE:

<223> OTHER INFORMATION: binding peptide

<400> SEQUENCE: 291

His Thr Asp Thr Ser Pro Gln
1               5

<210> SEQ ID NO 292
<211> LENGTH: 7
<212> TYPE: PRT
<213> ORGANISM: Artificial Sequence
<220> FEATURE:
<223> OTHER INFORMATION: binding peptide

<400> SEQUENCE: 292

Ser Pro Leu Tyr His Asp Arg
1               5

<210> SEQ ID NO 293
<211> LENGTH: 7
<212> TYPE: PRT
<213> ORGANISM: Artificial Sequence
<220> FEATURE:
<223> OTHER INFORMATION: binding peptide

<400> SEQUENCE: 293

Leu Lys Tyr Leu Glu Arg Asp
1               5

<210> SEQ ID NO 294
<211> LENGTH: 7
<212> TYPE: PRT
<213> ORGANISM: Artificial Sequence
<220> FEATURE:
<223> OTHER INFORMATION: binding peptide

<400> SEQUENCE: 294

Leu Ser Glu Ala Pro Gly Ile
1               5

<210> SEQ ID NO 295
<211> LENGTH: 7
<212> TYPE: PRT
<213> ORGANISM: Artificial Sequence
<220> FEATURE:
<223> OTHER INFORMATION: binding peptide

<400> SEQUENCE: 295

Glu Arg Gln Asn Asn Met Asn
1               5

<210> SEQ ID NO 296
<211> LENGTH: 7
<212> TYPE: PRT
<213> ORGANISM: Artificial Sequence
<220> FEATURE:
<223> OTHER INFORMATION: binding peptide

<400> SEQUENCE: 296

Asn Ala Phe Glu Ser Leu Phe
1               5

<210> SEQ ID NO 297
<211> LENGTH: 7
<212> TYPE: PRT
<213> ORGANISM: Artificial Sequence
<220> FEATURE:
<223> OTHER INFORMATION: binding peptide

```
<400> SEQUENCE: 297

Cys Tyr Ile Pro Thr Pro Arg
 1               5

<210> SEQ ID NO 298
<211> LENGTH: 7
<212> TYPE: PRT
<213> ORGANISM: Artificial Sequence
<220> FEATURE:
<223> OTHER INFORMATION: binding peptide

<400> SEQUENCE: 298

Asn Ser Tyr Asn Ser Gly Leu
 1               5

<210> SEQ ID NO 299
<211> LENGTH: 7
<212> TYPE: PRT
<213> ORGANISM: Artificial Sequence
<220> FEATURE:
<223> OTHER INFORMATION: binding peptide

<400> SEQUENCE: 299

Asp Pro Gln Ala Asn Leu Thr
 1               5

<210> SEQ ID NO 300
<211> LENGTH: 7
<212> TYPE: PRT
<213> ORGANISM: Artificial Sequence
<220> FEATURE:
<223> OTHER INFORMATION: binding peptide

<400> SEQUENCE: 300

Arg Gln Ala Asn Leu Thr Gln
 1               5

<210> SEQ ID NO 301
<211> LENGTH: 7
<212> TYPE: PRT
<213> ORGANISM: Artificial Sequence
<220> FEATURE:
<223> OTHER INFORMATION: binding peptide

<400> SEQUENCE: 301

Leu Asp Gln His Ser Met Lys
 1               5

<210> SEQ ID NO 302
<211> LENGTH: 7
<212> TYPE: PRT
<213> ORGANISM: Artificial Sequence
<220> FEATURE:
<223> OTHER INFORMATION: binding peptide

<400> SEQUENCE: 302

His Asn Met His Gln Ala Val
 1               5

<210> SEQ ID NO 303
<211> LENGTH: 7
<212> TYPE: PRT
<213> ORGANISM: Artificial Sequence
<220> FEATURE:
<223> OTHER INFORMATION: binding peptide

<400> SEQUENCE: 303
```

```
Leu Asn Thr Leu Leu Gly Thr
1               5

<210> SEQ ID NO 304
<211> LENGTH: 7
<212> TYPE: PRT
<213> ORGANISM: Artificial Sequence
<220> FEATURE:
<223> OTHER INFORMATION: binding peptide

<400> SEQUENCE: 304

Leu Leu Pro Arg Leu His Asp
1               5

<210> SEQ ID NO 305
<211> LENGTH: 7
<212> TYPE: PRT
<213> ORGANISM: Artificial Sequence
<220> FEATURE:
<223> OTHER INFORMATION: binding peptide

<400> SEQUENCE: 305

Pro His His Lys Met Gln Asn
1               5

<210> SEQ ID NO 306
<211> LENGTH: 7
<212> TYPE: PRT
<213> ORGANISM: Artificial Sequence
<220> FEATURE:
<223> OTHER INFORMATION: binding peptide

<400> SEQUENCE: 306

Pro Gly Glu Ala Arg Gly Glu
1               5

<210> SEQ ID NO 307
<211> LENGTH: 7
<212> TYPE: PRT
<213> ORGANISM: Artificial Sequence
<220> FEATURE:
<223> OTHER INFORMATION: binding peptide

<400> SEQUENCE: 307

Gly Ser His Ser Pro Pro Gln
1               5

<210> SEQ ID NO 308
<211> LENGTH: 7
<212> TYPE: PRT
<213> ORGANISM: Artificial Sequence
<220> FEATURE:
<223> OTHER INFORMATION: binding peptide

<400> SEQUENCE: 308

Lys Leu Gln Ala His Pro Asn
1               5

<210> SEQ ID NO 309
<211> LENGTH: 7
<212> TYPE: PRT
<213> ORGANISM: Artificial Sequence
<220> FEATURE:
<223> OTHER INFORMATION: binding peptide

<400> SEQUENCE: 309

Phe Thr Met Asn Asp Ile Arg
1               5
```

```
<210> SEQ ID NO 310
<211> LENGTH: 7
<212> TYPE: PRT
<213> ORGANISM: Artificial Sequence
<220> FEATURE:
<223> OTHER INFORMATION: binding peptide

<400> SEQUENCE: 310

Pro Ser Thr Thr Lys His Gly
1               5

<210> SEQ ID NO 311
<211> LENGTH: 7
<212> TYPE: PRT
<213> ORGANISM: Artificial Sequence
<220> FEATURE:
<223> OTHER INFORMATION: binding peptide

<400> SEQUENCE: 311

Asn Ser Thr Arg Thr Phe Ala
1               5

<210> SEQ ID NO 312
<211> LENGTH: 7
<212> TYPE: PRT
<213> ORGANISM: Artificial Sequence
<220> FEATURE:
<223> OTHER INFORMATION: binding peptide

<400> SEQUENCE: 312

Pro Ser His Thr Asn Val Asn
1               5

<210> SEQ ID NO 313
<211> LENGTH: 7
<212> TYPE: PRT
<213> ORGANISM: Artificial Sequence
<220> FEATURE:
<223> OTHER INFORMATION: binding peptide

<400> SEQUENCE: 313

Lys Pro Thr Phe Ile Arg Ala
1               5

<210> SEQ ID NO 314
<211> LENGTH: 7
<212> TYPE: PRT
<213> ORGANISM: Artificial Sequence
<220> FEATURE:
<223> OTHER INFORMATION: binding peptide

<400> SEQUENCE: 314

Asp Pro Arg Lys Ser Ala Gln
1               5

<210> SEQ ID NO 315
<211> LENGTH: 7
<212> TYPE: PRT
<213> ORGANISM: Artificial Sequence
<220> FEATURE:
<223> OTHER INFORMATION: binding peptide

<400> SEQUENCE: 315

Gly Leu Thr Arg His Gln Ala
1               5
```

```
<210> SEQ ID NO 316
<211> LENGTH: 7
<212> TYPE: PRT
<213> ORGANISM: Artificial Sequence
<220> FEATURE:
<223> OTHER INFORMATION: binding peptide

<400> SEQUENCE: 316

Ser Ala Ser Thr Pro Arg Ala
 1               5

<210> SEQ ID NO 317
<211> LENGTH: 4
<212> TYPE: PRT
<213> ORGANISM: Artificial Sequence
<220> FEATURE:
<223> OTHER INFORMATION: repeatable motif

<400> SEQUENCE: 317

Ile Asn Ala Gln
 1

<210> SEQ ID NO 318
<211> LENGTH: 4
<212> TYPE: PRT
<213> ORGANISM: Artificial Sequence
<220> FEATURE:
<223> OTHER INFORMATION: repeatable motif

<400> SEQUENCE: 318

Lys Thr Pro Ser
 1

<210> SEQ ID NO 319
<211> LENGTH: 4
<212> TYPE: PRT
<213> ORGANISM: Artificial Sequence
<220> FEATURE:
<223> OTHER INFORMATION: repeatable motif

<400> SEQUENCE: 319

Asn Ser Ser Ser
 1

<210> SEQ ID NO 320
<211> LENGTH: 4
<212> TYPE: PRT
<213> ORGANISM: Artificial Sequence
<220> FEATURE:
<223> OTHER INFORMATION: repeatable motif

<400> SEQUENCE: 320

Asn Thr Ser Pro
 1

<210> SEQ ID NO 321
<211> LENGTH: 4
<212> TYPE: PRT
<213> ORGANISM: Artificial Sequence
<220> FEATURE:
<223> OTHER INFORMATION: repeatable motif

<400> SEQUENCE: 321

Ser Asn Ala Thr
 1

<210> SEQ ID NO 322
<211> LENGTH: 5
```

```
<212> TYPE: PRT
<213> ORGANISM: Artificial Sequence
<220> FEATURE:
<223> OTHER INFORMATION: repeatable motif

<400> SEQUENCE: 322

Gln Ala Asn Leu Thr
 1               5

<210> SEQ ID NO 323
<211> LENGTH: 5
<212> TYPE: PRT
<213> ORGANISM: Artificial Sequence
<220> FEATURE:
<223> OTHER INFORMATION: repeatable motif

<400> SEQUENCE: 323

Thr Asn Pro Asn His
 1               5

<210> SEQ ID NO 324
<211> LENGTH: 4
<212> TYPE: PRT
<213> ORGANISM: Artificial Sequence
<220> FEATURE:
<223> OTHER INFORMATION: repeatable motif

<400> SEQUENCE: 324

Ala Asn Leu Thr
 1

<210> SEQ ID NO 325
<211> LENGTH: 4
<212> TYPE: PRT
<213> ORGANISM: Artificial Sequence
<220> FEATURE:
<223> OTHER INFORMATION: repeatable motif

<400> SEQUENCE: 325

Asn Pro Asn His
 1

<210> SEQ ID NO 326
<211> LENGTH: 4
<212> TYPE: PRT
<213> ORGANISM: Artificial Sequence
<220> FEATURE:
<223> OTHER INFORMATION: repeatable motif

<400> SEQUENCE: 326

Gln Ala Asn Leu
 1

<210> SEQ ID NO 327
<211> LENGTH: 4
<212> TYPE: PRT
<213> ORGANISM: Artificial Sequence
<220> FEATURE:
<223> OTHER INFORMATION: repeatable motif

<400> SEQUENCE: 327

Thr Asn Pro Asn
 1

<210> SEQ ID NO 328
<211> LENGTH: 4
<212> TYPE: PRT
<213> ORGANISM: Artificial Sequence
```

```
<220> FEATURE:
<223> OTHER INFORMATION: repeatable motif

<400> SEQUENCE: 328

Cys Ser Pro Met
 1

<210> SEQ ID NO 329
<211> LENGTH: 4
<212> TYPE: PRT
<213> ORGANISM: Artificial Sequence
<220> FEATURE:
<223> OTHER INFORMATION: repeatable motif

<400> SEQUENCE: 329

Cys Ser Pro Leu
 1

<210> SEQ ID NO 330
<211> LENGTH: 5
<212> TYPE: PRT
<213> ORGANISM: Artificial Sequence
<220> FEATURE:
<223> OTHER INFORMATION: repeatable motif

<400> SEQUENCE: 330

Cys Lys Thr Pro Ser
 1               5

<210> SEQ ID NO 331
<211> LENGTH: 4
<212> TYPE: PRT
<213> ORGANISM: Artificial Sequence
<220> FEATURE:
<223> OTHER INFORMATION: repeatable motif

<400> SEQUENCE: 331

Cys Thr Thr Thr
 1

<210> SEQ ID NO 332
<211> LENGTH: 4
<212> TYPE: PRT
<213> ORGANISM: Artificial Sequence
<220> FEATURE:
<223> OTHER INFORMATION: repeatable motif

<400> SEQUENCE: 332

Thr Thr Ala Cys
 1
```

PHENOLIC BINDING PEPTIDES

The present patent application is a continuation application of U.S. patent application Ser. No. 10/528,514, filed 9 Dec. 2005, which was a national stage entry of international patent application PCT/US03/31776, filed 6 Oct. 2003, which claimed priority of U.S. patent application Ser. No. 60/417,210, filed 8 Oct. 2002.

BACKGROUND OF THE INVENTION

The present invention relates to novel binding peptides and to binding peptide conjugates, wherein the binding peptide is linked to an agent. In particular the peptides bind to tannin, polyphenolic and/or anthocyanin compounds and more particularly to tea and wine stains. The invention also concerns the use of the binding peptides for delivering agents to targeted tannin, polyphenolic and/or anthocyanin compounds that comprise tea and wine stains.

Binding peptides and proteins conjugated to a binding peptide have numerous uses in many varied applications. Some of these uses include applications in enzymatic compositions, particularly detergent compositions, in personal care applications, in food industry applications, in diagnostic applications and therapeutic applications.

For example oxidative-reductase (redox) enzymes capable of modifying the color associated with colored compounds could be used more effectively if conjugated to a peptide that targeted a particular compound. For example, a peptide that binds to a tannin, polyphenolic or anthocyanin compound as a target on a fabric or on a surface such as ceramic could deliver the redox enzyme more effectively to the specific target and result in more effective bleaching of the stain. This selective targeting of a tannin, polyphenolic or anthocyanin compound can provide a significant improvement in the cleaning performance of enzymatic compositions. In another example, a peptide that binds to a tannin, polyphenolic or anthocyanin compound on a surface such as skin, teeth or nails could deliver the redox enzyme more effectively to the specifically targeted pigmented areas which then may result in bleaching of the area.

SUMMARY OF THE INVENTION

In a first aspect the invention concerns a peptide which binds to a compound selected from the group consisting of tannin, anthocyanin and phenolic compounds. In one preferred embodiment the binding peptide of the invention will bind to a tea or wine stain and particularly to a tea or wine stain on a fabric or on a surface such as ceramic, glass, wood, paper, metal, plastic, skin, teeth, hair or nails.

In a second aspect the invention relates to a binding peptide comprising an amino acid sequence shown in any one of SEQ ID NOs. 1-316 and a binding peptide having at least 70% sequence identity thereto. In a further aspect the invention relates to a binding peptide consisting essentially of an amino acid sequence shown in any one of SEQ ID NOs. 1-316 and a binding peptide having at least 70% sequence identity thereto. In one embodiment the binding peptides of the invention further comprise a cysteine amino acid residue at the N and C terminus of a peptide as shown in any one of SEQ ID NOs. 1-316 or a binding peptide having at least 70% sequence identity thereto. In a another embodiment, the binding peptide is selected from the group consisting of KTPSPHG (SEQ ID NO. 1); PNTTRHS (SEQ ID NO. 2); LWTSPQL (SEQ ID NO. 8); TNNTSPT (SEQ ID NO. 24); SPTSTNS (SEQ ID NO. 43); TTTTPFA (SEQ ID NO. 77); SWNTSPL (SEQ ID NO. 80); QAVKASHATMYL (SEQ ID NO. 97); SYDLIPPRSGLA (SEQ ID NO. 104); DPNTTSH (SEQ ID NO. 118); KASHLVP (SEQ ID NO: 132); LPTSTLT (SEQ ID NO. 139); QNQKSTT (SEQ ID NO. 158); SIIPPRQ (SEQ ID NO. 168); SNKPLSPNDLR (SEQ ID NO. 193) and peptides having at least 75% amino acid sequence identity thereto.

In a third aspect the invention concerns a binding peptide having a repeatable motif selected from the group consisting of LPL (SEQ ID NOs. 120, 123, 115 and 250); FAT (SEQ ID NOs. 125, 227 and 235); STT (SEQ ID NOs. 90, 158, 230 and 310); HSP (SEQ ID NOs. 18, 252 and 307); TNK (SEQ ID NOs. 40, 259 and 287); SPL (SEQ ID NOs. 53, 80, 152, 229, 232 and 292); THS (SEQ ID NOs. 62, 209 and 290); TSP (SEQ ID NOs. 8, 24, 80, 223 and 291); SPT (SEQ ID NOs. 24, 43 and 266); AQT (SEQ ID NOs. 59, 134 and 205); NSS (SEQ ID NOs. 31, 86, 213, 227 and 278); PAL (SEQ ID NOs. 109, 224 and 256); SGL (SEQ ID NOs. 104, 284 and 298); and TQT (SEQ ID NOs. 105, 281 and 287) and a binding peptide having at least 75% amino acid sequence identity thereto.

In a fourth aspect the invention concerns a binding peptide conjugate which comprises a binding peptide of the invention linked to an agent. In one embodiment the agent is a protein. In a preferred embodiment the protein is an enzyme and particularly an enzyme that catalyzes an oxidation-reduction reaction. In a particularly preferred embodiment the enzyme is selected from the group consisting of laccases, phenol oxidases, catalases, bilirubin oxidases, glucose oxidases and peroxidases. In one embodiment the binding peptide is covalently linked to said agent and in another embodiment the binding peptide and said agent are separated by a linker.

In a fifth aspect the invention relates to an enzymatic composition which comprises a binding peptide of the invention, an enzyme, and one or more surfactants. In one embodiment the composition is a detergent composition. In a second embodiment the enzymatic composition comprises a) a binding peptide conjugate which includes a binding peptide of the invention linked to an agent, wherein the agent is an enzyme and b) one or more surfactants. In a third embodiment the invention relates to a method for modifying a tea or wine stain on a fabric or a surface comprising contacting the fabric or surface having a tea or wine stain thereon with the enzymatic composition. Preferably the surface is ceramic, skin or teeth. Modification may include either removing the tea or wine stain or enhancing the tea or wine stain.

In a sixth aspect the invention relates to a method for delivering an agent to a target which comprises conjugating an agent with a binding peptide of the invention to form a binding peptide conjugate and exposing a target to the binding peptide conjugated, wherein the binding peptide conjugate binds to said target. In one embodiment the target is a tea or wine stain. In another embodiment the agent is an enzyme. In another embodiment the target is a tea or wine stain.

In a seventh aspect the invention relates to polynucleotide sequences encoding a binding peptide or a binding peptide conjugate according to the invention and to vectors and host cells comprising said polynucleotide sequences.

BRIEF DESCRIPTION OF THE DRAWINGS

FIGS. 1A-1B illustrate the amino acid sequences of peptides represented by SEQ ID NOs. 1-111 that bind to tea stains on cotton. A peptide string having an amino acid residue designated as X in a specific position indicates that the amino acid residue is not known and may be any L-amino acid.

FIGS. 2A-2B illustrate the amino acid sequences of peptides represented by SEQ ID NOs. 112-201 that bind to tea stains on ceramic. A peptide string having an amino acid residue designated as X in a specific position indicates that the amino acid residue is not known and may be any L-amino acid.

FIGS. 3A, 3B and 3C illustrate the amino acid sequences of peptides represented by SEQ ID NOs. (202-316) that bind to wine stains on cotton. A peptide string having an amino acid residue designated as X in a specific position indicates that the amino acid residue is not known and may be any L-amino acid.

DETAILED DESCRIPTION OF THE INVENTION

General Terms

Figure 4:
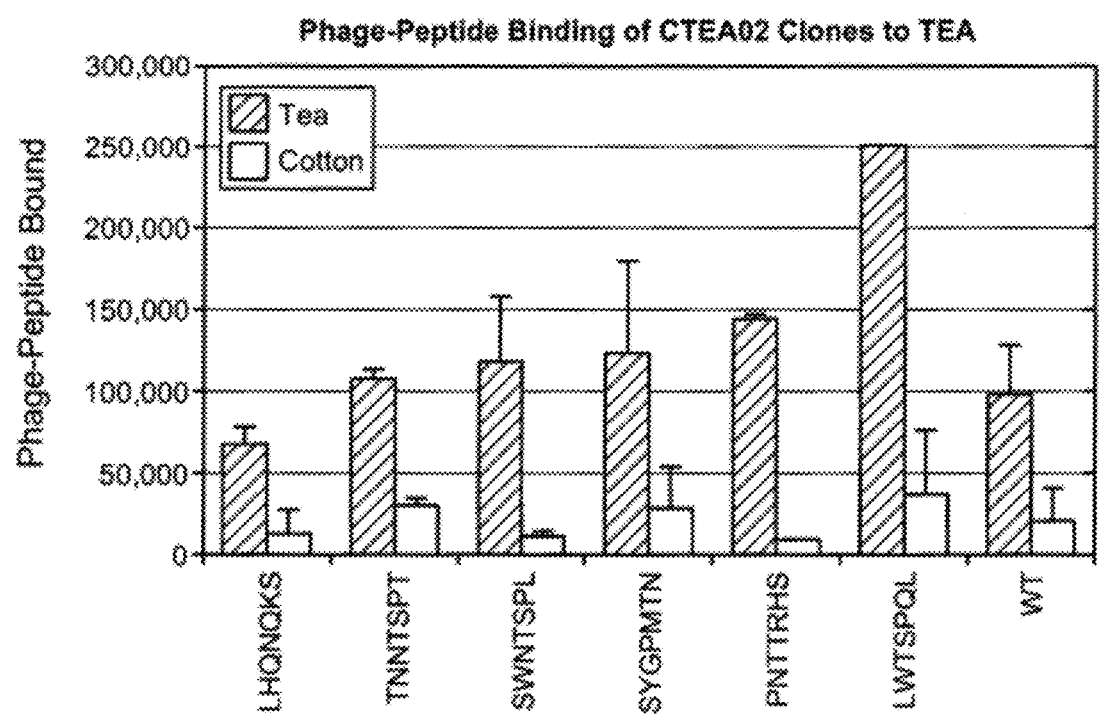
FIG. 4 illustrates the preferential binding of phage bound peptides (PNTTRHS (SEQ ID NO. 2); LWTSPQL (SEQ ID NO. 8); TNNTSPT (SEQ ID NO. 24); SYGPMTN (SEQ ID NO. 65); LHQNQKS (SEQ ID NO. 68); and SWNTSPL (SEQ ID NO. 80)) to tea stains on cotton swatches (■) compared to binding on non-stained cotton swatches (□). WT is a control, a phage without a binding peptide insert.

Unless defined otherwise, all technical and scientific terms used herein have the same meaning as commonly understood by one of ordinary skill in the art to which this invention pertains. For the purpose of the present invention, the following terms are used to describe the invention herein.

The term "peptide" refers to an oligomer in which the monomer units are amino acids (typically, but not limited to L-amino acids) linked by an amide bond. Peptides may be two or more amino acids in length. Peptides that are greater than 100 amino acids in length are generally referred to as polypeptides. However, the terms, peptide, polypeptide and protein may be used interchangeably. Standard abbreviations for amino acids are used herein and reference is made to Singleton et al., (1987) DICTIONARY OF MICROBIOLOGY AND MOLECULAR BIOLOGY, 2ND ED. page 35.

The term "isolated" as used herein refers to a nucleic acid or amino acid sequence that is removed from at least one component with which it is naturally associated.

"Percent sequence identity" with respect to peptide or polynucleotide sequences refers to the percentage of residues that are identical in the two sequences. Thus 95% amino acid sequence identity means that 95% of the amino acids in the sequences are identical. Percent identity can be determined by direct comparison of the sequence information provided between two sequences and can be determined by various commercially available computer programs such as BEST-FIT, FASTA, DNASTAR, TFASTA and BLAST.

A "binding peptide" according to the invention is a peptide that binds to a target with a binding affinity of at least about $10^{-2}$ M, at least about $10^{-3}$ M, at least about $10^{-4}$ M, at least about $10^{-5}$ M and preferably between about $10^{-2}$ M to $10^{-15}$ M, between about $10^{-2}$ M to $10^{-10}$ M and between about $10^{-2}$ M to $10^{-9}$ M.

The binding affinity of a peptide for its target or the binding affinity of a binding peptide conjugate for its target may be described by the dissociation constant ($K_D$). $K_D$ is defined by $k_{off}/k_{on}$. The $k_{off}$ value defines the rate at which a bound-target complex breaks apart or separates. This term is sometimes referred to in the art as the kinetic stability of the peptide-target complex or the ratio of any other measurable quantity that reflects the ratio of binding affinity such as an enzyme-linked immunosorbent assay (ELISA) signal. $K_{on}$ describes the rate at which the target and the binding peptide (or binding peptide conjugate) combine to form a bound-target complex.

In one aspect, the $k_{off}$ value for the bound-target complex will be less that about $10^{-2}$ sec$^{-1}$, less that about $10^{-3}$ sec$^{-1}$, less than about $10^{-4}$ sec$^{-1}$ and also less than about $10^{-5}$ sec$^{-1}$.

The term "conjugation" as used herein means an agent is chemically linked or joined directly or indirectly to a terminus of a binding peptide. The phrases "binding peptide conjugate" and "conjugated agent" are used interchangeably herein. A binding peptide conjugate or a conjugated agent may be considered a fusion protein. A fusion protein refers to a protein that comprises two separate and distinct regions that may or may not originate from the same protein.

An "agent" is any molecule or compound that is capable of being conjugated with a binding peptide of the invention and preferably capable of be chaperoned or delivered to a target. Agents according to the invention comprise a broad class of compounds including but not limited to proteins, carbohydrates, lipids, chemicals, such as dyes, bleaching compounds and fluorescent compounds, and ions, such as salts.

Selectivity is defined herein as enhanced binding of a binding peptide to a target compared to the binding of the peptide to a non-target. Selectivity may also be defined as the enhanced binding of a conjugated agent to a target compared to the binding of a non-conjugated agent to the same target. Selectivity may be in the range of about 1.25:1 to 25:1; about 1.5:1 to 15:1; about 1.5:1 to 10:1; and about 1.5:1 to 5:1. Preferably the selectively is at least 4:1, 3:1 or 2:1 for either a) the binding of a binding peptide to a target compared to the binding of the peptide to a non-target or b) the binding of a conjugated agent to a target compared to the binding of the non-conjugated agent to the same target.

Preferred targets of a binding peptide or a binding peptide conjugate of the invention are tannin, phenolic or anthocyanin compounds. Particularly tannin, phenolic or anthocyanin compounds found in tea or wine, and particularly a tea and/or wine stain. However, the target compounds may be found on a material, surface or solution.

A stain is defined herein as a colored compound which undergoes a redox chemical reaction when exposed to certain classes of enzymes, for example phenol oxidizing enzymes such as laccases. A coloured compound is a substance that adds colour to a textile or to substances which result in the visual appearances of stains. Targeted classes of coloured substances which may appear as a stain include the following;

a) porphyrin derived structures, such as heme in blood stain or chlorophyll in plants;

b) tannins and polyphenols (see P. Ribéreau-Gayon, Plant Phenolics, Ed. Oliver & Boyd, Edinburgh, 1972, pp. 169-198) which occur in tea, wine, coffee, chocolate, cola, banana and peach stains;

c) carotenoids and carotenoid derivatives, which are the red, orange and yellow pigments occurring in fruits and vegetables such as tomato, mango, carrots, paprika and leafy green vegetables. Commonly known carotenoids include alpha and beta-carotene, lycopene, lutein, zeaxanthin, and cryptoxantin. These compounds include the oxygenated carotenoids, xanthophylls. Reference is made to G. E. Bartley et al., The Plant Cell (1995), Vol. 7, 1027-1038, Biochemical Nomenclature and Related Documents, 2nd Ed. Portland Press (1992), pages 226-238, and Pure Appl. Chem, (1974) 41:407-431);

d) anthocyanins, the highly coloured molecules which occur in many fruits and flowers, such as red grapes, cranberries, blueberries and cherries and red wine (P. Ribéreau-Gayon, Plant Phenolics, Ed. Oliver & Boyd, Edinburgh, 1972, 135-169); and e) Maillard reaction products, the yellow/brown coloured substances which appear upon heating of mixtures of carbohydrate molecules in the presence of protein/peptide structures, such as found in cooking oil.

A coloured compound may also be a dye that may be incorporated into a fiber by chemical reaction, adsorption or dispersion. Examples include direct Blue dyes, acid Blue dyes, reactive Blue dyes, and reactive Black dyes.

A stain may occur on a fabric or other surface material. Nonlimiting examples of fabric include, cotton, wool, silk, polyester, rayon, linen, nylon and blends thereof. Nonlimiting examples of a surface material include, ceramic, glass, wood, paper, metal, plastic, stainless steel, teeth, bone, nails, skin and hair.

The phrase "modify the colour associated with a coloured compound" means that the coloured compound is changed through oxidation-reduction, either directly or indirectly, such that the colour appears modified i.e. the colour visually appears to be increased; decreased; changed from one color to another, such as from blue to red; decoloured; bleached; or removed; particularly bleached.

As used in the specification and claims, the singular "a", "an" and "the" include the plural references unless the context clearly dictates otherwise. For example, the term a host cell may include a plurality of host cells.

The following references describe the general techniques employed herein: Sambrook et al (1989) MOLECULAR CLONING: A LABORATORY MANUAL, Cold Spring Harbour Laboratory Press, Cold Spring Harbour, N.Y.; and Ausubel et al. (1987) CURRENT PROTOCOLS IN MOLECULAR BIOLOGY, Greene-Publishing & Wiley Interscience NY (Supplemented through 1999). The contents of all references, patents and published patent applications cited throughout this application are hereby incorporated by reference in their entirety.

B. Binding Peptides

The binding peptides of the invention may be obtained and identified using methods well known in the art. These methods may include the use of random peptide libraries, synthetic peptide libraries, peptide loop libraries, antibody libraries and protein libraries. Many of these library collections are commercially available. Screening techniques may include yeast display, ribosome display, biopanning and acid elution. Once a library is screened, the peptides that bind to a specific target may be identified by various well-known means in the art including but not limited to acid elution, polymerase chain reaction (PCR), sequencing, and the like. These techniques are described in various references such as Cwirla et al., (1990) *Proc. Natl. Acad. Sci. USA* 87:6378; Parmley et al., (1988) *Gene* 73:305; Balass et al., (1996) *Anal. Biochem.*, 243:264; Huls et al., (1996) *Nature Biotechnol.*, 7:276 and WO 01/79479).

A typical method for selecting binding peptides of the invention involves removing from a library those peptides that bind non-specifically to a material and then incubating the remaining members of the library with a stained material containing the target substrate.

Once selected a binding peptide may be identified, amplified or produced in bulk by any one of a number of standard techniques. For example the peptide may be produced recombinantly using genetic engineering or the peptide may be chemically synthesized.

Preferably the binding peptides of the invention are between 4 and 50 amino acids in length, also between 4-25 amino acids in length, between 4-20 amino acids in length and between 6-15 amino acids in length.

The binding peptides according to the invention include the peptides listed in FIGS. 1A-1B (SEQ ID NOs. 1-111), FIGS. 2A-2B (SEQ ID NOs. 112-201); and FIGS. 3A, 3B and 3C (SEQ ID NOs. 202-316. These peptides bind to molecules found in tea and/or wine.

The invention further includes binding peptides having at least 60% but less than 100% amino acid sequence identity to a binding peptide listed in FIGS. 1A, 1B, 2A, 2B, 3A, 3B or 3C (SEQ ID NOs. 1-316). For example at least 65%, at least 70%, at least 75%, at least 80%, at least 85%, at least 90%, at least 93%, at least 95%, at least 97%, at least 99% amino acid sequence identity. A peptide having at least 60% sequence identity to a binding peptide listed in FIGS. 1A, 1B, 2A, 2B, 3A, 3B or 3C will also have a binding affinity for the same target in the range of $10^{-2}$M to $10^{-15}$M, generally at least about $10^{-2}$M, at least about $10^{-3}$M, at least about $10^{-4}$M and at least about $10^{-5}$M. In one embodiment a binding peptide according to the invention will have no more than 2 amino acid residues that differ from a binding 7-mer peptide which is listed in FIGS. 1A, 1B, 2A, 2B, 3A, 3B or 3C. In another embodiment, a binding peptide according to the invention will have no more than 3 amino acid residues that differ from a binding 12-mer peptide which is listed in FIGS. 1A, 1B, 2A, 2B, 3A, 3B or 3C.

In one embodiment, preferred binding peptides of FIGS. 1A-1B are: KTPSPHG (SEQ ID NO. 1); PNTTRHS (SEQ ID NO. 2); KTPSSME (SEQ ID NO. 5); LWTSPQL (SEQ ID NO. 8); SLNNTNT (SEQ ID NO. 11); QKHSPGH (SEQ ID NO. 18); TNNTSPT (SEQ ID NO. 24); QTQPPGS (SEQ ID NO. 25); TMAPAKN (SEQ ID NO. 36); SHLDKRL (SEQ ID NO. 37); TTTNKPL (SEQ ID NO. 40); SPTSTNS (SEQ ID NO. 43); PGSNATQ (SEQ ID NO. 44); SQDTPMY (SEQ ID NO. 45); TDPSMMN (SEQ ID NO. 46); GQADRLQ (SEQ ID NO. 47); TPQRLLT (SEQ ID NO. 48); SQMSPLH (SEQ ID NO. 53); TQNPTHS (SEQ ID NO. 62); HGSSAHP (SEQ ID NO. 64); TTAAPQM (SEQ ID NO. 70); SSNLPFA (SEQ ID NO. 71); TTTTPFA (SEQ ID NO. 77); SWNTSPL (SEQ ID NO. 80); PSPPTNQ (SEQ ID NO. 82); PLTSTQP (SEQ ID NO. 85); HVSDLAG (SEQ ID NO. 87); TLSRTTA (SEQ ID NO. 88); HLRSTTD (SEQ ID NO. 90); SPMQPRL (SEQ ID NO. 93); FTANLRA (SEQ ID NO. 94); LFLPPTPPPEPL (SEQ ID NO. 96); QAVKASHATMYL (SEQ ID NO. 97); ETQPSAMGGSSL (SEQ ID NO. 99); STSWPPQPHLSP (SEQ ID NO. 102); SYDLIPPRSGLA (SEQ ID NO. 104); NTTQTLRHVSLA (SEQ ID NO. 105); TSGFDRALSPSL (SEQ ID NO. 107); SNSTMNALAPA (SEQ ID NO. 111) and peptides having at least 70% amino acid sequence identity thereto.

Particularly preferred binding peptides of FIGS. 1A and 1B are PNTTRHS (SEQ ID NO. 2); LWTSPQL (SEQ ID NO. 8); TNNTSPT (SEQ ID NO. 24); and SWNTSPL (SEQ ID NO. 80) and peptides having at least 75% amino acid sequence identity thereto.

In another embodiment, preferred binding peptides of FIGS. 2A-2B are:
ALGXIPXTAHQW (SEQ ID NO. 114); ARSIQPF (SEQ ID NO. 115); ATVILTD (SEQ ID NO. 116); DPNTTSH (SEQ ID NO. 118); FLPLLTL (SEQ ID NO. 120); FQLIPTG (SEQ ID NO. 121); GVPFATP (SEQ ID NO. 125); IPTTRQT (SEQ ID NO. 131); KASHLVP (SEQ ID NO. 132); KDPSWPSQAQTP (SEQ ID NO. 134); LPTSTLT (SEQ ID NO. 139); PPSPLTP (SEQ ID NO. 152); PTLAGAS (SEQ ID NO. 154); QDTAPLT (SEQ ID NO. 157); QNQKSTT (SEQ ID NO. 158); QPGHLDI (SEQ ID NO. 159); LSLPMQ (SEQ ID NO. 164); SIIPPRQ (SEQ ID NO. 168); SSLLPRS (SEQ ID NO. 174); TAPLISI (SEQ ID NO. 177); TKTTWQT (SEQ ID NO. 180); TLFYTKX (SEQ ID NO. 181); TQRLTTH (SEQ ID NO. 182); TSLVPDK (SEQ ID NO. 184); WQLARPK (SEQ ID NO. 191); WQTXLTD (SEQ ID NO.

192); WSNKPLSPNDLR (SEQ ID NO. 193); YTKTSQY (SEQ ID NO. 201); and peptides having at least 70% amino acid sequence identity thereto.

In another embodiment preferred binding peptides of FIGS. 1A, 1B, 2A and 2B include KTPSPHG (SEQ ID NO. 1); PNTTRHS (SEQ ID NO. 2); LWTSPQL (SEQ ID NO. 8); TNNTSPT (SEQ ID NO. 24); SPTSTNS (SEQ ID NO. 43); TTTTPFA (SEQ ID NO. 77); SWNTSPL (SEQ ID NO. 80); QAVKASHATMYL (SEQ ID NO. 97); SYDLIPPRSGLA (SEQ ID NO. 104); DPNTTSH (SEQ ID NO. 118); KASHLVP (SEQ ID NO. 132); LPTSTLT (SEQ ID NO. 139); QNQKSTT (SEQ ID NO. 158); SIIPPRQ (SEQ ID NO. 168); WSNKPLSPNDLR (SEQ ID NO. 193) and peptides having at least 75% amino acid sequence identity thereto.

In another embodiment, preferred binding peptides of FIGS. 3A, 3B and 3C are: QYHGPLP (SEQ ID NO. 203); TGNSSQQ (SEQ ID NO. 213); LPLQPLMPPLNQ (SEQ ID NO. 225); NSSPFATMPNAL (SEQ ID NO. 227); NVN-NHIH (SEQ ID NO. 247); ADRLRPT (SEQ ID NO. 251); HSPQMQS (SEQ ID NO. 252); SPALVNS (SEQ ID NO. 256); TNKIPPL (SEQ ID NO. 259); TNPNHIM (SEQ ID NO. 260); QPLKTKQ (SEQ ID NO. 262); TKSPTAI (SEQ ID NO. 266); KSPEYPF (SEQ ID NO. 270); TTQTNKD (SEQ ID NO. 287); PATNPNH (SEQ ID NO. 289); SPLY-HDR (SEQ ID NO. 292); NAFESLF (SEQ ID NO. 296); DPQANLT (SEQ ID NO. 299); RQANLTQ (SEQ ID NO. 300); LDQHSMK, (SEQ ID NO. 301); PSTTKHG (SEQ ID NO. 310); and peptides having at least 70% amino acid sequence identity thereto.

In a further embodiment, the binding peptides according to the invention may include cysteine residues on each end of the peptide. These binding peptides are more specifically referred to herein as binding peptide C-C derivatives. The cysteine residues form a disulfide bridge, making the peptide form a loop on the surface of the phage. Thus, if the binding peptide is used as an internal replacement or insert for protein loops or turns, the binding peptide may be used in the C-C derivative form or the non C-C derivative form. Particularly preferred C-C derivative peptides are those comprising 7 amino acids. In one aspect preferred C-C derivatives are the preferred 7-mers disclosed in FIGS. 1A-1B; FIGS. 2A-2B and FIGS. 3A, 3B and 3C as designated above.

Additionally, a linker (L) molecule (also sometimes referred to as a spacer moiety in the prior art) may be added to either end of a binding peptide (P), for example, L-P or P-L. The linker molecule may enhance the binding of the peptide to its target. A linker molecule may be any carbon containing compound, such as a short peptide, for example, the amino acid triad GGH or GGHGG; a carbon chain, for example, $(CH_2)_n$ wherein n equals 1 to 10; a polymer, for example PEG $(CH_2-O)_n$ wherein n equals 2-20; a sugar; a lipid or the like.

As stated above, the linker molecule may be attached to the binding peptide alone or the linker molecule may be part of the binding peptide conjugate. For example, when the linker (L) is placed between the binding peptide (P) and the agent (A), (A-L-P) or when the linker is attached to the peptide at the non-conjugated end, (A-P-L). A linker molecule may be attached to any of the binding peptides represented as SEQ ID NOs. 1-316 of FIGS. 1A, 1B, 2A, 2B, 3A, 3B and 3C.

Repeatable motifs have been observed in a number of the binding peptides listed in FIGS. 1A, 1B, 2A, 2B, 3A, 3B and 3C. Repeatable motifs include at least three consecutive amino acid residues in a peptide string and may include four, five or six consecutive amino acid residues that are found in at least two of the binding peptides listed in FIGS. 1A, 1B, 2A, 2B, 3A, 3B and 3C.

Preferred repeatable motifs which are included in binding peptides listed in FIGS. 1A and 1B, which bind to a tea stain are: INAQ, KTPS, NSSS, NTSP, SNAT, GSS, HQT, PGS, SSS, TPQ, TQP, TSP, TTA, TTT, APA, HQG, HPS, HVS, KPL, LNN, LPF, SNS, SPL, SPM, SPT, SRL, LSP, LSR, MMN, MYL, NAQ, NNT, NPT, NTT, PAK, PFA, PLH, PPP, PPT, PQM, PSL, PSP, PTH, QKH, RLQ, SLA, SNA, TQK, TQM, TQN, TSG, TST, STM, STR, TAA, TDP, TMA, TTP, TTQ, VTT, AND QNQ.

Particularly preferred repeatable motifs and peptides which include these motifs of FIGS. 1A and 1B are INAQ, (SEQ ID NOs. 59 and 84); KTPS, (SEQ ID NOs. 1 and 5); NSSS, (SEQ ID NOs. 31 and 86); NTSP, (SEQ ID NOs. 24 and 80); SNAT, (SEQ ID NOs. 32 and 44); GSS, (SEQ ID NOs. 64, 99 and 100); HQT, (SEQ ID NOs. 7, 15 and 108); PGS, (SEQ ID NOs. 25, 44 and 100); TPQ, (SEQ ID NOs. 14, 48 and 66); TQP, (SEQ ID NOs. 25, 85 and 99); TSP, (SEQ ID NOs. 8, 24 and 80) and TTA, (SEQ ID NOs. 28, 70 and 88).

Preferred repeatable motifs which are included in binding peptides listed in FIGS. 2A and 2B which bind to a tea stain are: ATP, APL, HPP, IPT, ISI, KTSQ, LPR, LPM, LPL, LPT, LST, LTD, LTP, LVP, LSP, PLI, PPR, PAP, PTL, PLT, SLV, SWP, TSQ, TAPL, TLF, TLT, TKT, WQT, and YTK.

Particularly preferred repeatable motifs and peptides which include these motifs of FIGS. 2A and 2B are LTP, (SEQ ID NOs. 142, 152 and 163) and LSP, (SEQ ID NOs. 137, 176 and 193).

Preferred repeatable motifs which are included in binding peptides listed in FIGS. 3A, 3B and 3C which bind to a wine stain are: QANLT; TNPNH; ANLT; NPNH; QANL; TNPN; PPL; SPL; AAT; ANL; DRL; ELP; FAT; GLS; HAM; HGP; HQA; HSP; KSP; KTK; LHD; LPL; LPP; LYH; MPN; MQS; NAF; NHI; NLT; NMN; NPN; NTL; NVN; NSS; PAL; PAT; PHP; PLM; PLN; PLP; PNH; PTA; PYT; QPL; QTN; RLH; RSA; SGL; SHS; SLF; SPQ; SRS; STP; STS; STT; TAE; TFA; TGN; THS; TKH; TNK; TNP; TPP; TPR; TQT; TRS; TSP; TTI; VNS; WNA; and YPF.

Particularly preferred repeatable motifs and peptides which include these motifs of FIGS. 3A, 3B and 3C are QANLT (SEQ ID NOs. 299 and 300); TNPNH (SEQ ID NOs. 260 and 289); ANLT (SEQ ID NOs. 300 and 299); NPNH (SEQ ID NOs. 260 and 289); QANL (SEQ ID NOs. 299 and 300); TNPN (SEQ ID NOs. 260 and 289); NSS (SEQ ID NOs, 213, 227 and 278); PPL (SEQ ID NOs. 225, 229 and 259) and SPL (SEQ ID NOs. 229, 232 and 292).

Preferred repeatable motifs for peptides that bind to compounds in wine and tea and binding peptides including these repeatable motifs are the following: LPL (SEQ ID NOs. 120, 123, 115 and 250); FAT (SEQ ID NOs. 125, 227 and 235); STT (SEQ ID NOs. 90, 158, 230 and 310); HSP (SEQ ID NOs. 18, 252 and 307); TNK (SEQ ID NOs. 40, 259 and 287); SPL (SEQ ID NOs. 53, 80, 152, 229, 232 and 292); THS (SEQ ID NOs. 62, 209 and 290); TSP (SEQ ID NOs. 8, 24, 80, 223 and 291); SPT (SEQ ID NOs. 24, 43 and 266); AQT (SEQ ID NOs. 59, 134 and 205); NSS (SEQ ID NOs. 31, 86, 213, 227 and 278); PAL (SEQ ID NOs. 109, 224 and 256); SGL (SEQ ID NOs. 104, 284 and 298); and TQT (SEQ ID NOs. 105, 281 and 287).

The repeatable motif may also include a cysteine residue at the beginning and/or end of the motif, non-limiting examples include (C)SPM, (C)SPL, (C)KTPS, (C)TTT, TTA(C) and the like.

In general, the repeatable motifs may occur alone in a binding peptide, as multiple motifs in the same binding peptide, in sequential order, or overlapping one another. For example the binding peptide KTPSPHG (SEQ ID NO: 1) includes the repeatable motif KTPS. The binding peptide LG TPQQT (SEQ ID NO: 14) includes the repeatable motif TPQ. The binding peptides RQANLTQ (SEQ ID NO. 300) and DPQANLT (SEQ ID NO. 299) include the repeatable motif QANLT. The binding peptides TTAAPQM (SEQ ID NO. 70) and ETQPSAMGGSSL (SEQ ID NO. 99) include two repeatable motifs, in the same sequence. The binding peptide LPLOPLMPPLNQ (SEQ ID NO. 225) includes two repeatable motifs LPL and QPL in sequential order.

Peptides, other than the binding peptides illustrated in FIGS. 1A, 1B, 2A, 2B, 3A, 3B and 3C, which have a repeatable motif as disclosed herein above are referred to herein as "homologous motif binding peptides". Homologous motif binding peptides will include 6-25 amino acid residues, preferably 6-15 amino acid residues and more preferably 6 to 12 amino acid residues. Further a homologous motif binding peptide will bind to a target with a binding affinity similar to or greater than the binding affinity to the same target as a binding peptide of FIGS. 1A, 1B, 2A, 2B, 3A, 3B or 3C having the same repeatable motif. Preferably the target will be a tannin, phenolic or anthocyanin compound, most preferably a tea or wine stain, and the binding affinity will be at least about $10^{-2}$M, at least about $10^{-3}$M, at least about $10^{-4}$M, at least about $10^{-6}$M and generally between about $10^{-2}$M and $10^{-9}$M.

A homologous motif binding peptide will include not only a repeatable motif as defined herein, but also will have between 20% and 95% amino acid sequence identity with a sequence illustrated in FIGS. 1A, 1B, 2A, 2B, 3A, 3B and 3C having the same repeatable motif, that is at least 25% sequence identity, at least 30% sequence identity, at least 40% sequence, at least 50% sequence identity, at least 60% sequence identity, at least 70% sequence identity, at least 80% sequence identity, at least 85% sequence identity, at least 90% sequence identity or at least 95% sequence identity to a binding peptide illustrated in FIGS. 1A, 1B, 2A, 2B, 3A, 3B and 3C which includes the same repeatable motif. Preferably if the homologous motif binding peptide is a 7 amino acid residue peptide, the homologous motif binding peptide will have at least 30% sequence identity with a binding peptide illustrated in FIGS. 1A, 1B, 2A, 2B, 3A, 3B and 3C having the same repeatable motif when the peptides are aligned with no gaps. If the homologous motif binding peptide is a 12 amino acid residue peptide, the peptide will have at least 25% sequence identity with a binding peptide illustrated in FIGS. 1A, 1B, 2A, 2B, 3A, 3B and 3C having the same repeatable motif when the peptides are aligned with no gaps.

C. Polynucleotides Encoding the Binding Peptides

The present invention encompasses polynucleotides which encode binding peptides according to the invention. Specifically polynucleotides include nucleic acid sequences encoding peptides illustrated in FIGS. 1A, 1B, 2A, 2B, 3A, 3B and 3C (SEQ ID NOs. 1-316) and their C-C derivatives. Additionally, polynucleotides of the invention will encode binding peptides having at least 70% amino acid sequence identity to a peptide illustrated in FIGS. 1A, 1B, 2A, 2B, 3A, 3B or 3C (SEQ ID NOs. 1-316), their C-C derivatives and homologous motif binding peptides. As will be understood by the skilled artisan, due to the degeneracy of the genetic code, a variety of polynucleotides can encode a binding peptide of the invention. The present invention encompasses all such polynucleotides. A polynucleotide which encodes a binding peptide of the invention may be obtained by standard procedures known in the art, for example, by chemical synthesis, by PCR and by direct isolation and amplification.

D. Conjugation of Binding Peptides to an Agent.

In one embodiment, a binding peptide conjugate is formed wherein a binding peptide according to the invention is linked with an agent. While agents may include proteins, carbohydrates, lipids and ions as described above, various preferred agents are listed below.

In one aspect an agent may be a protein. The protein may be an enzyme, a hormone, a growth factor, a cytokine, an antibody, and an anti-astringent protein or other protein.

Enzymes include but are not limited to amylolytic enzymes, proteolytic enzymes, cellulolytic enzymes, redox enzymes, transferases and cell wall degrading enzymes. Examples of these enzymes include, but are not limited to, amylases, proteases, xylanases, lipases, laccases, phenol oxidases, oxidases, such as glucose oxidases and galactoses, oxidases, peroxidases, cutinases, catalases, cellulases, hemicellulases, esterases, pectinases, glycosidases, isomerases, transferases, galactosidases, pullulanases, epimerases, phytases, hydroxylases, epoxydases, alkyltransferases and chitinases.

Hormones include, but are not limited to, follicle-stimulating hormone, luteinizing hormone, corticotropin-releasing factor, somatostatin, gonadotropin hormone, vasopressin, oxytocin, erthropoietin, insulin and the like.

Growth factors are proteins that bind to receptors on the cell surface, with the primary result of activating cellular proliferation and/or differentiation. Growth factors include, but are not limited to, platelet-derived growth factors, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 ($\alpha$ and $\beta$), IL-2 through IL-13) and the interferons ($\alpha$, $\beta$ and $\gamma$).

Antibodies include, but are not limited to, immunoglobulins from any species from which it is desirable to produce large quantities. It is especially preferred that the antibodies are human antibodies. Immunoglobulins may be from any class, i.e., G, A, M, E or D.

Anti-astringency compounds include proteins or carbohydrates that reduce the astringency of other compounds by either binding to them and/or precipitating them. Anti-astringency proteins include but are not limited to casein and albumin.

The agent may also be a vitamin, such as thiamin, riboflavin, niacin, pantothenic acid, pyridoxal, pyridoxamine, pyridoxine, biotin, cobalamin, folic acid, ascorbic acid, vitamin A, vitamin D, vitamin E and vitamin K.

Sweeteners which may be agents include carbohydrates and sugar alcohols such as, raw sugar, corn sweetener, corn syrup, dextrose, sucrose, granulated sugar, brown sugar, confectioner's sugar, honey, lactose, maltose, mannitol, sorbitol, aspartame.

An agent may be a bleaching compound, such as an oxygen bleaching agent or halogen bleaching agent. Non-limiting examples of oxygen bleaching agents include perborate, percarbonate, sulfate/hydrogen peroxide, and percarboxylic acid. Non-limiting examples of halogen bleaching agents include hypohalite and hypochlorite bleaching agents such as trichloro-isocyanuric acid, sodium and potassium dichloro-isocyanurate and N-chloro and N-bromo alkanesulphonamides. Ions such as salts for example potassium, calcium and bicarbonates may also be agents.

An agent may also be a dye such as a fluorescent dye. For example, fluorescein isothiocynate (FITC), rhodamine, phycoerytherin, phycocyanin, fluorescamine and green fluorescent protein (GFP). Fluorescent dyes are disclosed in British Patent Appl. No. 2094826.

Particularly preferred agents are proteins such as enzymes. In one embodiment preferred enzymes are oxidoreductase enzymes. These enzymes include dehydrogenases, reductases, oxidases, synthases, monooxygenases, isomerases, lipoxygenases, dioxygenases and hydroxylases. More specifically preferred oxidoreductase enzymes as agents include laccases (EC 1.10.3.2), phenol oxidases (EC 1.14.18.1), catalases (EC 1.11.1.6), bilirubin oxidases (EC 1.3.3.5), catechol oxidases (EC 1.10.3.1), peroxidases (EC 1.11.1.7), and glucose oxidases (EC 1.1.3.4). Other preferred enzymes include amylases, proteases, xylanases, lipases, transferases and cellulases.

Numerous references are available on suitable enzymes which may be linked with a binding peptide according to the invention to form a binding peptide conjugate. Proteins conjugated with a binding peptide of the invention may be recombinant proteins or naturally occurring proteins. Oxidoreductase enzymes, such as phenol oxidizing enzymes and particularly laccases, and polynucleotides encoding said enzymes which may be conjugated with a binding peptide of the invention are disclosed for example in WO 98/27197; WO 98/27198; WO 98/38286; WO 99/49020; WO 00/37654; WO 01/21809; U.S. Pat. Nos. 4,760,025; 5,770,419; 5,985,818; 6,060,442; and 6,168,936. Proteases, such as subtilisins are disclosed in U.S. Pat. Nos. 6,197,567; 6,190,900; 6,110,884; EP 130756; EP 251446; EP 260105; EP525610; WO 87/04461 and WO 94/02618. Cellulases are disclosed in U.S. Pat. Nos. 5,989,899; 6,063,611; 6,268,328; 6,287,839 and 6,423,524. Amylases are disclosed in U.S. Pat. No. 6,440,716. Lipases are disclosed in U.S. Pat. No. 6,156,552; EP 407225; WO 95/06720; WO 95/22615; and WO 96/27002.

A binding peptide of the invention may act to deliver an agent to a target. The term deliver or delivering means to assist in the movement of the agent. In one embodiment the agent, particularly an enzyme, is delivered to a compound selected from tannin, polyphenolic or anthocyanin compounds and most particularly a tannin, polyphenolic or anthocyanin stain on a fabric or surface.

E. Making the Binding Peptide Conjugate.

The binding peptide conjugate may be constructed by methods well known in the art including use of PCR. A binding peptide according to the invention may be inserted into an agent or attached to a terminus of the agent. When the agent is a protein a) the binding peptide may be inserted into the protein b) the binding peptide may replace an internal loop or turn, and/or c) the binding agent may be attached to the carbon or nitrogen terminus of the enzyme. In a preferred embodiment the agent is a protein (particularly an enzyme) and the binding peptide is linked to the carbon terminus of the agent. An agent may also be linked to a binding protein by chemical modification such as by an ester linkage or an amide linkage. Various methods of conjugating peptides to an agent are disclosed for example in U.S. Pat. No. 6,348,317; WO 02/57299; WO 02/55543; WO 02/26782; WO 00/48464; and WO 98/34956.

F. Expression Systems Transformation and Cultivation of Host Cells.

The present invention provides vectors, host cells, expression methods and systems for the production of the binding peptides and binding peptide conjugates in host microorganisms, such as bacteria, fungus and yeast.

Molecular biology techniques are disclosed in Sambrook et al., MOLECULAR BIOLOGY CLONING: A LABORATORY MANUAL, 2nd Ed (1989) Cold Spring Harbor Laboratory Press, Cold Spring Harbor, N.Y. A polynucleotide encoding a binding peptide or a binding peptide conjugate is obtained and transformed into a host cell using appropriate vectors. A variety of vectors and transformation and expression cassettes suitable for the cloning, transformation and expression of proteins in fungus, yeast and bacteria are known by those of skill in the art.

Vectors will further include initiation control regions or promoters, which are useful to drive expression of the binding peptide or binding peptide conjugates in a host cell. Regulatory control elements are known to those skilled in the art. Virtually any promoter capable of driving the expression of the particular agent is suitable for the present invention. Once suitable cassettes are constructed they are used to transform a host cell.

Preferably a host cell is a microbial host cell, and preferably a bacteria, fungal or yeast host cell. In one embodiment the host cell is a gram positive bacteria, preferably a *Bacillus* species, such as *B. subtilis*. In another embodiment the host cell is a gram negative host cell, preferably an *Escherichia* species, such as *E. coli*. In other embodiments the host cell is fungal host cell, such as a filamentous fungus including a *Aspergillus* species, a *Trichoderma* species and a *Mucor* species. Particularly preferred are *T. reesei*, *A. niger* and *A. oryzae*.

One skilled in the art is well aware of methods of transforming host cells with polynucleotides encoding a protein of interest. General transformation procedures are taught in CURRENT PROTOCOLS IN MOLECULAR BIOLOGY (vol. 1, edited by Ausubel et al., John Wiley & Sons, Inc. 1987, Chapter 9) and include calcium phosphate methods, transformation using PEG and electroporation. For *Aspergillus* and *Trichoderma*, PEG and calcium mediated protoplast transformation can be used (Finkelstein, D B 1992 TRANSFORMATION. IN BIOTECHNOLOGY OF FILAMENTOUS FUNGI. TECHNOLOGY AND PRODUCTS (eds. by Finkelstein & Bill) 113-156. Electroporation of protoplast is disclosed in Finkelestein, D B 1992 Transformation. In BIOTECHNOLOGY OF FILAMENTOUS FUNGI. TECHNOLOGY AND PRODUCTS (eds. by Finkelstein & Bill) 113-156. Microprojection bombardment on conidia is described in Fungaro et al. (1995) Transformation of *Aspergillus nidulans* by microprojection bombardment on intact conidia. *FEMS Microbiology Letters* 125 293-298. *Agrobacterium* mediated transformation is disclosed in Groot et al. (1998) *Agrobacterium tumefaciens*-mediated transformation of filamentous fungi. *Nature Biotechnology* 16 839-842. For transformation of *Saccharomyces*, lithium acetate mediated transformation and PEG and calcium mediated protoplast transformation as well as electroporation techniques are known by those of skill in the art.

Transformation of *Bacillus* is described, for example in Chang and Cohen (1979) *Mol. Gen. Genet.* 168:111-115; Smith et al. (1986) *Appl. and Env. Microbiol.* 51:634; Mann et al. (1986) *Current Microbiol.* 13: 131-135. Also general reference is made to MOLECULAR BIOLOGICAL METHODS FOR BACILLUS. Eds. Hardwood and Cutting, John Wiley & Sons (1990).

A binding peptide or a binding peptide conjugate, particularly an enzyme conjugate wherein the enzyme is an oxidoreductase, a protease, an amylase, a xylanase, a lipase or a cellulase, may be produced by cultivation of a host cell which includes a polynucleotide encoding the binding peptide or enzyme conjugate, under aerobic conditions in nutrient media containing assimilable carbon and nitrogen together with other essential nutrient. These conditions are well known in the art.

Host cells that comprise a coding sequence for a binding peptide or binding peptide conjugate and express the binding peptide may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

Once a binding peptide conjugate is encoded the enzyme conjugate may be isolated and purified from the host cell by well-known techniques such as, cell separation and concentration of the cell free broth by ultrafiltration, ammonium sulfate fractionation, purification by gel filtration, ion exchange or hydrophobic interaction chromatography, PEG extraction and crystallization.

Methods of purification are well-known for many enzymes. One non-limiting example of purification of an enzyme conjugated to a binding peptide of the invention includes small-scale purification (e.g., less than 1 g) of the enzyme using hydrophobic interaction chromatography. Samples may be filtered and loaded onto a column containing 20HP2 resin (Perceptives Biosystems), hooked up to a Bio-Cad workstation (Perceptives Biosystems). The column may be washed with ammonium sulfate in buffer. Elution of the derivatized phenol oxidizing enzyme activity can be performed using a salt gradient ranging from 35% to 0% of a 3M ammonium sulfate solution in 30 mM Mes Bis Tris Propane buffer at pH 5.4. The fractions enriched in the derivatized phenol oxidizing enzyme activity can be monitored using UV absorbance at 280 nm and a qualitative ABTS (2,2'-azino-bis (3-ethylbenzothiazoline-6-sulfonate) activity assay. The samples can be pooled, concentrated and diafiltered against water. Enzyme samples purified according to this method are estimated to be at least about 70% pure.

G. Applications

The binding peptides and binding peptide conjugates according to the invention may be used in numerous applications which include but are not limited to enzyme and cleaning compositions, food industry applications and personal care applications. Some of these applications are discussed below, but the specific examples should not be interpreted as limiting any general application.

Enzyme and Detergent Compositions.

A binding peptide conjugate of the present invention may be used to produce, for example, enzymatic compositions for use in detergent or cleaning compositions; such as for removing food stains on fabrics or removing food stains on surfaces such as ceramic and teeth.

Enzymatic compositions may also comprise additional components, such as for example, for formulation or as performance enhancers. For example, detergent compositions may comprise, in addition to the binding peptide conjugate, conventional detergent ingredients such as surfactants, builders and enzymes. Surfactants include nonionic, anionic and cationic surfactants (see EP-A-346995). Enzymes include for example, proteases, amylases, lipases, cutinases, cellulases and peroxidases (U.S. Pat. No. 4,689,297). Other ingredients include enhancers, stabilizing agents, bactericides, optical brighteners and perfumes. The enzymatic compositions may take any suitable physical form, such as a powder, an aqueous or non-aqueous liquid, a paste or a gel. Reference is made to U.S. Pat. No. 3,929,678; U.S. Pat. Nos. 4,760,025; 5,011,681; WO 97/04079; WO 97/076202; WO 96/06930; WO 95/01426 and McCutheon's Detergents and Emulsifiers, North American Ed. (1986) Allured Publishing Co.

A binding peptide conjugate, particularly when the agent is an enzyme and more particularly when the agent is a redox enzyme such as a laccase, can act to modify the color associated with dyes or colored compounds in the presence or absence of enhancers depending upon the characteristics of the colored compound. If a compound is able to act as a direct substrate for the binding peptide conjugate, the phenol oxidizing enzyme will modify the color associated with a dye or colored compound in the absence of an enhancer, although an enhancer may still be preferred for optimum phenol oxidizing enzyme activity. For other colored compounds unable to act as a direct substrate for the binding peptide conjugate or not directly accessible to the conjugate, an enhancer may be required for optimum enzyme activity and modification of the color.

Enhancers are described in for example WO 95/01426, WO 96/06930, and WO 97/11217. Enhancers include but are not limited to phenothiazine-10-propionic acid (PTP), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate (ABTS), 2,6 dimethoxyphenol (2,6-DMP), and guaiacol (2-methoxyphenol).

While enzymes and their use in detergent and cleaning compositions are well known, a main advantage of a binding peptide conjugate according to the invention is the delivery of an agent to a target and the enhanced binding of the conjugate to a target stain compared to the agent without the binding peptide.

Food Industry Applications.

Tannins are important taste components in tea and wine. In wine, tannins come from the skin and seed of red grapes and from the wooden oak barrels used in the fermentation and aging process. Tannins, which can bind to proteins in saliva, cause the proteins to precipitate and result in a stringent or bitter taste. Various tannins are found in wine during the early stages of the fermentation process. During the later stages of the fermentation process many of these tannins are extracted from the wine. A binding peptide or a binding peptide conjugate according to the invention may be particularly useful in this wine aging process. By targeting a tannin compound in the early stage of the wine fermentation process the astringency of tannins could be reduced or eliminated in the wine.

Personal Care Applications.

Tannins and anthocyanin compounds are natural dyes and may act as ultraviolet light protectants, tan enhancers and astringents. By either direct addition of tannin or anthocyanin binding peptides, which may displace tannins or anthocyanins from the compounds they bind, or by addition of a binding peptide conjugate one could modify the action of these compounds on various biological tissues particularly teeth, nails and skin. A non-limiting example includes a conjugated binding peptide comprising a peptide linked to a bleaching agent, wherein the conjugate delivers the bleaching agent to stained teeth for the purpose of bleaching. Another non-limiting example includes providing a binding peptide to the skin wherein astringency may be modified. Personal care products including a binding peptide may be formulated as creams, lotions, ointments and the like.

Having thus described the binding peptides and binding peptide conjugates of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of percent weight per volume (w/v). As used herein, dilutions, quantities, etc., which are expressed in terms of % (v/v), refer to percentage in terms of volume per volume. Temperatures referred to herein are given in degrees centigrade (C).

EXPERIMENTAL

Example 1

Selection of the Binding Peptides on Tea and Wine Stained Cotton

While a number of selection techniques may be used to screen for binding peptides, the majority of the binding peptides according to the invention were selected according to the method described herein below.

10 microliters of a commercially (New England Biolabs) available phage display library either a cyclic 7-mer (at $2 \times 10^3$ pfu/ml) or a linear 12-mer (at $4 \times 10^{12}$ pfu/ml) were pre-incubated with a cotton swatch in a pre-blocked and washed 96 well plate in the presence of a 150 µl Tris-buffered saline (TBS) solution (at $2 \times 10^{-5}$ g/l for the cyclic 7-mer, $2 \times 10^{-3}$ g/l for the linear 12-mer) of detergent, pH 10 for 20 minutes using gentle shaking. The solution was pipetted off and added to a second cotton swatch for 20 minutes under gentle shaking. This process was repeated a third time. The solution was pipetted off and added to a tea or wine stained cotton swatch (Textile Innovators Corp. Windsor, N.C.) for 60 minutes under gentle agitation. The solution was drawn off and discarded. The stained swatch was washed 5 times for 5 minutes each with 200 µl of TBST (TBS containing 0.1% Tween 20). The swatch was transferred to an empty well using sterile tips, washed as described above, and transferred to another empty well. 15 µl of a glycine 0.2M solution pH 2.2 was added to the stained swatch and the plate was shaken for less than 10 minutes. This solution was neutralized by the addition of 100 µl of a Tris HCL 1 M solution, pH 9.1 for 10 minutes. The solution, which constitutes the acid eluted peptide population, was pipetted off and stored at 4° C. until further use.

Example 2

Amplification of the Acid Eluted Peptides

4×20 µl of the acid eluted phage peptide population was used to infect 4×400 µl E. coli (New England BioLabs) grown to an OD at 610 nm of 0.3 to 0.65 from a 100× dilution in LB of an overnight culture. The cells were plated on 4×140 mm LB plates in the presence of IPTG (Sigma) (40 µl at 20 mg/ml per plate) and Xgal (Sigma) (40 µl at 40 mg/ml of DMF per plate), added to 5 mls of melted top agarose, and left to incubate overnight at 37° C. The 4 plates were scraped with a sterile glass microscope slide and the scrapings were pushed through an 18.5 gage needle of a 60 ml syringe into a sterile conical tube; 50 ml of TBS was added to the tube and the capped tube was left to shake on a rocker at room temperature for at least 14 hrs. The contents of the tube were centrifuged at 10,000 rpm for 30 minutes in sterile Oakridge tubes at 4° C. The supernatant was collected and the phage precipitated by adding ⅙ volume of a 20% polyethylene glycol (PEG)/2.5 M NaCl solution. This was left to incubate at 4° C. for at least 4 hours and preferably overnight. The solution was then spun at 10,000 rpm for 30 minutes at 4° C. and the supernatant discarded. The pellet was resuspended in 1 ml of TBS and transferred to a sterile Eppendorff tube. The phage was reprecipitated with ⅙ volume of a 20% PEG/2.5 M NaCl solution with incubation on ice for at least 1 hour. This was followed by another centrifugation at 10,000 rpm for 10 min at 4° C. The supernatant was discarded, the tube re-spun briefly, and residual supernatant removed. The pellet was resuspended in 200 µl TBS/0.02% $NaN_3$, spun to remove insoluble material and transferred.

Example 3

Biopanning

The amplified phage peptide populations from the first round of deselection on cotton/selection of stained cotton swatches were submitted to another round of deselection and selection as described above. For the cyclic 7-mer peptide library $2 \times 10^{-4}$ g/l TBS was used, and for the linear 12-mer peptide library $2 \times 10^{-2}$ g/l TBS was used. After acid elution and amplification of the phage, a third round of biopanning was performed. The third round used $2 \times 10^{-3}$ g/l TBS of detergent for the cyclic 7-mer phage peptides and $2 \times 10^{-1}$ g/l TBS for the linear 12-mer phage peptides. After acid elution and amplification, a fourth round of biopanning was used and 2 g/l of detergent dissolved in water in one experiment and TBS in another were used for both types of phage peptides. The phage peptides were acid eluted and amplified from the fourth round of biopanning and selected in a fifth round of biopanning wherein the Tween 20 concentration was increased from 0.1% to 0.8% in the wash conditions. Additionally a round of selection on tea and wine was performed using the phage peptides from the third round as described above. In this fourth round of biopanning, 2 g/l of detergent in water in the wash conditions was used. One skilled in the art is well aware that various parameters as described hereinabove may be varied without affecting the nature of the invention. The above described method is one method which may be used to screen for binding peptides of the invention.

Example 4

Selection of the Binding Peptides on Stained Cotton after Biopanning

225 µl of a ¹⁄₁₀₀ dilution of an overnight culture of E. coli cells in LB broth were incubated with phage plaques using sterile toothpicks in a sterile 96-well V-bottom plate. A replica plate was made for glycerol stocks of the phage peptides. The plates were covered with porous Qiagen plate sealers and shaken for 4 hours at 37° C. at 280 rpm in a humidified shaker box and then spun at 4000 rpm for 30 min at 4° C. 160 µl of the phage peptides supernatant was transferred to another 96-well V-bottom plate containing 64 µl of 20% PEG/2.5 M NaCl. The plates were left to shake for 5 minutes and then left to stand for 10 minutes. The glycerol stock plate was prepared by adding 100 µl phage supernatant to 150 µl 75% glycerol solution in a sterile 96 well plate which was then sealed with parafilm, labeled, and stored at −70° C. until further use.

The PEG precipitated phage plate was centrifuged at 4000 rpm for 20 minutes at 4° C. The plate was inverted rapidly to remove excess PEG/NaCl and left upside down on a clean paper towel to drain residual fluid. 60 µl of iodide salt solution (10 mM Tris.HCl, pH 8.0, 1 mM EDTA, 4 M NaI) were added to each well and the phage pellets thoroughly resuspended by shaking the plate vigorously for 5 minutes. 150 µl of 100% EtOH were added and the plate was spun at 4000 rpm for 20 minutes at 4° C., the supernatants discarded and the plate blotted. The pellets were washed with 225 µl of 70% EtOH without disturbing the pellets; the plate was inverted and left to air-dry for at least 30 minutes. The pellets were resuspended in 30 µl of Tris.HCl 10 mM, pH 8.5 buffer by shaking the plate for 30 minutes at full speed. 1 µl of g96 reverse primer (obtained from New England BioLabs, 3.4 pmole per tube) was added to 11 µl of DNA pellet sample and the contents submitted for sequencing on a ABI Applied Biosystem 373XL.

By raising the concentration of detergent in every round of biopanning and additionally during the washes, the stringency of the selection and wash steps was increased. In so doing, only those peptides that bind specifically to compounds in tea or wine remain bound after successive selection/wash steps in increasing detergent concentrations. Accordingly, increasing concentration of detergent between biopanning rounds, improves the number of phage that contains real peptide binders, and reduces the number of false-positives. Thus this approach helps improve the signal to noise ratio in this biopanning procedure.

FIGS. 1A-1B and 3A-3C (SEQ ID NOs.1-111 and 206-316) illustrate the amino acid sequences of numerous binding peptides determined according to the method described in examples 1-4.

Example 5

Selection of the Phage Binding Peptides on Tea Stained Ceramic

Deselection as described above was performed three times on unstained pieces of a ceramic teapot in a blocked 96 well plate using either cyclic 7-mer, linear 7-mer, and or linear 12-mer phage peptide libraries in the presence of a commercially available dish detergent. Selection was then performed on tea stained pieces of ceramic. The tea stained ceramic pieces were rinsed in TBST. After acid elution and neutralization, the tea stained ceramic pieces were further rinsed in TBS, dried and placed in PCR tubes. Lysis buffer was added to the tea stained ceramic and lysis was performed. The lysis solutions were subjected to a series of PCR reactions, TA cloning and sequencing as described above. The peptides were analyzed for the presence of repeatable motifs. Additionally, the PCR products in the TA cloning step were amplified using PCR. The PCR fragments were digested with restriction enzymes and the resulting fragments were purified using standard phenol/chloroform extraction and ethanol precipitation procedures. The fragments were eluted on a 8% PA gel in TBE and fragments of interest were cut out with a razor blade and further purified using the Qiagen purification kit procedure. The purified fragments were ligated with vector and competent E. coli E2537 cells were transformed using well known techniques. The transformants were sequenced according to standard protocols and the corresponding phage peptide libraries amplified prior to a second round of selection and deselection.

Using amplified phage peptide libraries from the first round of selection, another round of deselection and selection was performed as described above. The tea stained ceramic pieces were rinsed with TBST prior to acid elution and neutralization. The pieces were then rinsed in TBS and dried. The phage peptide libraries bound to the tea stained ceramic were lyzed and their DNA amplified using a series of PCR reactions. TA cloning was preformed on the PCR products. The TA clones were picked for PCR and sequenced as described previously herein. The sequences were also analyzed for the presence of repeatable motifs.

FIGS. 2A-2B (SEQ ID NOs. 112-201) illustrate the amino acid sequence of numerous binding peptides determined according to the method described in this example 5.

Example 6

Selective Binding of Phage Bound Peptides to Tea Stained Cotton Swatches

The phages containing the peptides LHQNQKS (SEQ ID NO. 68), TNNTSPT (SEQ ID NO. 24), SWNTSPL (SEQ ID NO. 80), SYGPMTN (SEQ ID NO. 65), PNTTRHS (SEQ ID NO. 2), LWTSPQL (SEQ ID NO. 8), and WT phage (without a peptide insert) were amplified from the glycerol stocks described in example 4. The amplification procedure was done as described as in example 2. A drop of corresponding glycerol stock was added to 20 ml of LB broth containing 0.2 ml of an overnight culture of E. coli. The culture was left to grow at 37° C. under vigorous shaking for 4.5 hrs, transferred to sterile 50 ml Oakridge tubes and centrifuged at 10 000 rpm for 10 min. The supernatants (17 mls) were added to fresh, sterile centrifuge tubes containing 3 ml of 20% PEG/2.5M NaCl solution (⅙ volume). The phages were precipitated at 4° C. for at least 4 hr and then centrifuged for 15 min at 10,000 rpm at 4° C. The phage pellets were suspended in 1 ml of TBS, transferred to sterile 1.5 ml microfuge tubes and re-precipitated with ⅙ volume PEG/NaCl on ice for at least 1 hr. The tubes were again spun for 10 min at 4° C. and supernatants discarded. The pellets were suspended in 0.2 ml of TBS/0.02% $NaN_3$ solution and the solutions were spun for 1 min to remove any insoluble material. Supernatants were transferred to sterile screw cap tubes.

Small (⅛") swatches of tea stained cotton (Textile Innovators Corp. Windsor, N.C.) and unstained cotton were punched out (in duplicates for each phage peptide) and placed in a pre-blocked and washed multititer plate. 0.150 ml of a 10× dilution of each titered phage peptide solution in detergent/TBS (0.001 g of detergent/L of TBS) was added to two tea stained swatches and to two unstained cotton swatches and left to incubate for 30 min at room temperature on a rocker, under mild agitation. Solution was pipetted off and the swatches were rinsed 9 times with 0.2 ml of a TBST solution. Swatches were transferred into fresh empty wells and rinsed another 9 times with 0.2 ml of a TBS solution. Each swatch was placed in a PCR tube. 0.1 ml of lysis buffer was added (10 mM Tris.HCl, pH8.4, 0.1% Triton X100), and then subjected to lysis at 95° C. for 10 min. 2 µl of a 100× dilution in lysis buffer (of the contents of each PCR tube) were added to Light Cycle™ (Roche) capillaries. 10 µl of the Light Cycler™ cocktail (Roche. Per tube: 5.3 ul water, 1.1 ul of $MgCl_2$, 1.2 µl of mix (ATP+ dye), 2.4 ul of primers) was added to the tubes and the contents briefly spun on a table top centrifuge. The capillary tubes were capped and run on the Light Cycler™ PCR instrument. The contents of the tubes were quantified against a series of dilutions of a known and quantified phage peptide standard. The fluorescent signal coming from the intercalating dye correlates to the amount of DNA (copies) (using melting point correction) and therefore number of phage peptide present.

FIG. 4 shows selective binding of phage-bound peptides to tea stained cotton swatches as compared to non-stained cotton swatches. For each phage-bound peptide illustrated, the peptide binds to tea stained cotton at least 2 times greater than to non-stained cotton. The graph shows phage peptide sequences which contain repeatable motifs bind greater than WT. LWTSPQL (SEQ ID NO. 8) binds to tea stained cotton about 2.5 times more than WT binds to tea stained cotton. LWTSPQL (SEQ ID NO. 8) binds to tea stain about 5 times more than to non-stained cotton. PNTTRHS (SEQ ID NO. 2) binds to tea stain about 15 times more than non-stained cotton.

The invention claimed is:

1. A method for delivering an agent to a tea stain on a fabric or a surface, comprising:
   a) conjugating the agent with a binding peptide consisting essentially of the amino acid sequence LWTSPQL (SEQ ID NO. 8) to form a binding peptide conjugate, and
   b) exposing the tea stain on the fabric or surface to the binding peptide conjugate,
   wherein the binding peptide conjugate binds to the tea stain on a fabric or surface.

2. The method of claim 1, wherein the agent is a polypeptide.

3. The method of claim 1, wherein the agent is an enzyme.

4. The method of claim 1, wherein the agent is an enzyme that catalyzes an oxidation-reduction reaction and is selected from the group consisting of laccases, phenol oxidases, catalases, bilirubin oxidases, glucose oxidases, and peroxidases.

5. The method of claim 1, wherein the agent is covalently linked to the peptide.

6. The method of claim 1, wherein the agent and peptide are separated by a linker.

7. The method of claim 1, wherein the exposing step is performed in the presence of one or more surfactants.

8. The method of claim 1, wherein the exposing step is performed in the presence of a detergent composition.

9. A method for delivering an agent to a tea stain on a fabric or a surface, comprising:
   exposing the tea stain on the fabric or surface to a binding peptide conjugate, wherein the binding peptide conjugate comprises the agent conjugated with a binding peptide consisting essentially of the amino acid sequence LWTSPQL (SEQ ID NO. 8),
wherein the binding peptide conjugate binds to the tea stain on a fabric or surface.

10. The method of claim 9, wherein the agent is a polypeptide.

11. The method of claim 9, wherein the agent is an enzyme.

12. The method of claim 9, wherein the agent is an enzyme that catalyzes an oxidation-reduction reaction and is selected from the group consisting of laccases, phenol oxidases, catalases, bilirubin oxidases, glucose oxidases, and peroxidases.

13. The method of claim 9, wherein the agent is covalently linked to the peptide.

14. The method of claim 9, wherein the agent and peptide are separated by a linker.

15. The method of claim 9, wherein the exposing step is performed in the presence of one or more surfactants.

16. The method of claim 9, wherein the exposing step is performed in the presence of a detergent composition.

* * * * *